United States Patent
Yurkovetskiy et al.

(10) Patent No.: US 8,524,214 B2
(45) Date of Patent: Sep. 3, 2013

(54) POLYAL DRUG CONJUGATES COMPRISING VARIABLE RATE-RELEASING LINKERS

(75) Inventors: Aleksandr Yurkovetskiy, Littleton, MA (US); Mao Yin, Needham, MA (US); Gui Liu, Lexington, MA (US); Laura C. Akullian, Belmont, MA (US); John J. Kane, Queens Village, NY (US); Cheri A. Stevenson, Haverhill, MA (US); Charles E. Hammond, Billerica, MA (US); Russell C. Petter, Stow, MA (US); John H. Van Duzer, Georgetown, MA (US); Timothy B. Lowinger, Carlisle, MA (US)

(73) Assignee: Mersana Therapeutics, Inc., Cambridge, MA (US)

( * ) Notice: Subject to any disclaimer, the term of this patent is extended or adjusted under 35 U.S.C. 154(b) by 344 days.

(21) Appl. No.: 12/789,047

(22) Filed: May 27, 2010

(65) Prior Publication Data

US 2010/0305149 A1 Dec. 2, 2010

Related U.S. Application Data

(60) Provisional application No. 61/181,926, filed on May 28, 2009.

(51) Int. Cl.
| | | |
|---|---|---|
| *A61K 31/045* | (2006.01) | |
| *A61K 31/04* | (2006.01) | |
| *A61K 31/13* | (2006.01) | |
| *A61K 31/21* | (2006.01) | |
| *A61K 31/33* | (2006.01) | |
| *A61K 31/695* | (2006.01) | |
| *A61K 31/765* | (2006.01) | |

(52) U.S. Cl.
USPC ............ 424/78.3; 525/417; 514/63; 514/185; 514/183; 514/188; 514/277; 514/280; 514/283; 514/359; 514/449; 514/451; 514/453; 514/510; 514/579; 514/724; 514/740

(58) Field of Classification Search
USPC ................... 514/63, 185, 183, 188, 227, 280, 514/283, 359, 449, 451, 453, 510, 579, 724, 514/740; 525/417; 424/78.3
See application file for complete search history.

(56) References Cited

U.S. PATENT DOCUMENTS

2002/0103136 A1   8/2002   Feng
2007/0190018 A1*  8/2007   Papisov .................. 424/78.3

OTHER PUBLICATIONS

Bose et al. (Bioorganic and Medicinal Chemistry, vol. 14, Issue 14, pp. 4694-4703, Published 2006).*
Conrad et al. (Journal of Medicinal Chemistry, vol. 22, No. 4, pp. 391-400, Published 1979).*
Tong et al., "Anticancer Polymeric Nanomedicines," Polymer Reviews, vol. 47: 345-381 (2007).
International Search Report issued for PCT/US10/36413, dated Sep. 20, 2010 (3 pages).
Conrad et al., "Structure-Activity Relationships of Dimeric Catharanthus Alkalois. 2. Experiemental Antitumor Activities of N-Substituted Deacetylvinblastine Amid (Vindesine) Sulfates 1-3"J. Med. Chem., vol. 22: 391-400 (1979).
Sapra, P. et al., "Novel Delivery of SN38 Markedly Inhibits Tumor Growth in Xenografts, Inlcluding a Camptothecin-11-Refractory Model," Clin. Cancer Res., 14: 1888-1896 (2008).
Barnett et al. "Structure-Activity Relationship of Dimeric Catharanthus Alkaloids." *J. Med. Chem.* 21.1(1978):88-96.

* cited by examiner

*Primary Examiner* — Richard Schnizer
*Assistant Examiner* — Alma Pipic
(74) *Attorney, Agent, or Firm* — Mintz Levin Cohn Ferris Glovsky and Popeo, P.C.; Heidi A. Erlacher; Lian Ouyang

(57) ABSTRACT

Polyal-Drug conjugates comprising a variable rate-releasing linker are described along with methods of making such conjugates. Uses for such Polyal-Drug conjugates is also described.

30 Claims, 13 Drawing Sheets

POLYAL DRUG CONJUGATES COMPRISING VARIABLE RATE-RELEASING LINKERS

PRIORITY

This application claims the benefit of U.S. Provisional Application No. 61/181,926, filed May 28, 2009. The entire disclosure of that application is relied on and incorporated into this application by reference.

INCORPORATION BY REFERENCE

Throughout this application, various publications are referenced. The disclosures of these publications in their entireties are hereby incorporated by reference into this application in order to more fully describe the state of the art as known to those skilled therein as of the date of the invention described and claimed herein.

This patent disclosure contains material that is subject to copyright protection. The copyright owner has no objection to the facsimile reproduction by anyone of the patent document or the patent disclosure, as it appears in the U.S. Patent and Trademark Office patent file or records, but otherwise reserves any and all copyright rights whatsoever.

FIELD

This application is directed to polymer-drug conjugates. In particular, this application is directed to polyal-drug conjugates comprising variable rate-releasing linkers, methods for using the same, and methods for designing the same.

BACKGROUND

Traditionally, pharmaceuticals have primarily consisted of small molecules that are dispensed orally (as solid pills and liquids) or as injectables. Over the past three decades, however, sustained release formulations (i.e., compositions that control the rate of drug delivery and allow delivery of the therapeutic agent at the site where it is needed) have become increasingly common and complex. Nevertheless, many questions and challenges regarding the development of new treatments, as well as the mechanisms with which to administer them, remain to be addressed.

Although considerable research efforts in this area have led to significant advances, drug delivery methods/systems that have been developed over the years and are currently used, still exhibit specific problems that require some investigating. For example, many drugs exhibit limited or otherwise reduced potencies and therapeutic effects because they are generally subject to partial degradation before they reach a desired target in the body. Once administered, sustained release medications deliver treatment continuously, e.g. for days or weeks, rather than for a short period of time (hours or minutes). One objective in the field of drug delivery systems, is to deliver medications intact to specifically targeted areas of the body through a system that can control the rate and time of administration of the therapeutic agent by means of either a physiological or chemical trigger. The rate of release of a drug from a polymeric conjugate can play a very significant role in altering the properties of the released drug, including having effects on the overall efficacy of the released drug, the duration of action of the released drug, the frequency of dosing required, the toxicity of the released drug, the biodistribution of the released drug, and the overall pharmacokinetic and pharmacodynamic properties of the released drug. For example, a slow, continuous release of a drug from a polymeric conjugate can mimic the effect of a slow, continuous infusion of the drug. Such a delivery can be beneficial, for example, with a drug-release product which has an inherently short-half life, and therefore would require much more frequent dosing if administered directly. Furthermore, a polymer conjugate of a drug release product could be designed to alter the $C_{max}$ of a drug-release product; by carefully designing a polymer conjugate with an appropriate release half-life, one can target a $C_{max}$ value such that it falls within a desired therapeutic window, for example, lower than a value known to have an associated toxicity, while maintaining a therapeutic level of the drug-release product.

Over the past decade, materials such as polymeric microspheres, polymer micelles, soluble polymers and hydrogel-type materials have been shown to be effective in enhancing drug targeting specificity, lowering systemic drug toxicity, improving treatment absorption rates, and providing protection for pharmaceuticals against biochemical degradation, and thus have shown great potential for use in biomedical applications, particularly as components of drug delivery devices.

The design and engineering of biomedical polymers (e.g., polymers for use under physiological conditions) are generally subject to specific and stringent requirements. In particular, such polymeric materials must be compatible with the biological milieu in which they will be used, which often means that they show certain characteristics of hydrophilicity. They also have to demonstrate adequate biodegradability (i.e., they degrade to low molecular weight species. The polymer fragments are in turn metabolized in the body or excreted, leaving no trace).

Biodegradability is typically accomplished by synthesizing or using polymers that have hydrolytically unstable linkages in the backbone. The most common chemical functional groups with this characteristic are esters, anhydrides, orthoesters, and amides. Chemical hydrolysis of the hydrolytically unstable backbone is the prevailing mechanism for the degradation of the polymer. Biodegradable polymers can be either natural or synthetic. Synthetic polymers commonly used in medical applications and biomedical research include polyethyleneglycol (pharmacokinetics and immune response modifier), polyvinyl alcohol (drug carrier), and poly(hydroxypropylmethacrylamide) (drug carrier). In addition, natural polymers are also used in biomedical applications. For instance, dextran, hydroxyethylstarch, albumin and partially hydrolyzed proteins find use in applications ranging from plasma substitute, to radiopharmaceutical to parenteral nutrition. In general, synthetic polymers may offer greater advantages than natural materials in that they can be tailored to give a wider range of properties and more predictable lot-to-lot uniformity than can materials from natural sources. Synthetic polymers also represent a more reliable source of raw materials, one free from concerns of infection or immunogenicity. Methods of preparing polymeric materials are well known in the art. However, synthetic methods that successfully lead to the preparation of polymeric materials that exhibit adequate biodegradability, biocompatibility, hydrophilicity and minimal toxicity for biomedical use are scarce. The restricted number and variety of biopolymers currently available attest to this.

Therefore, a need exists in the biomedical field for low-toxicity, biodegradable, biocompatible, hydrophilic polymer conjugates comprising pharmaceutically useful modifiers, which overcome or minimize the above-referenced problems, and which can release their drug cargo (the corresponding drug-release product) at appropriate rates. Such polymer conjugates would find use in several applications, including components for biomedical preparations, pharmaceutical formulations, medical devices, implants, and the packaging/delivery of therapeutic, diagnostic and prophylatic agents.

SUMMARY

In one aspect, conjugates of Formula I are described:

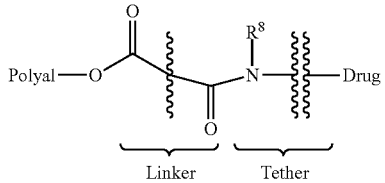

wherein

Polyal is a polyacetal or polyketal;

Linker is a dicarboxylic acid moiety containing two or more atoms between the carbonyls and present two or more atoms between the carbonyl groups;

Tether is a bifunctional organic moiety comprising a secondary or tertiary amine and a second functional group;

$R_a$ is H, alkyl, or together with a $CH_2$ of the backbone of the Tether forms a five- or six-membered ring; and Drug is any organic compound with a molecular weight of between about 200 daltons and 1000 daltons, capable of covalent attachment to the Tether and; presents the covalent attachment of Drug to Tether via the second functional group of Tether;

wherein when Linker is a dicarboxylic acid with two atoms between the carbonyls and Tether contains a nitrogen with no reactive hydrogen, the release half-life of Drug is from about 10 h to more than about 300 h;

when Linker is a dicarboxylic acid with at least three atoms between the carbonyls and contains a heteroatom alpha to the carbonyl forming the ester, the release half-life is less than about 10 hours;

when Linker is a dicarboxylic acid with at least three atoms between the carbonyls with no heteroatom alpha to the carbonyl forming the ester, the release half-life is more than about 100 hours;

when Linker is a dicarboxylic acid with two atoms between the carbonyls and Tether contains a nitrogen with a reactive hydrogen the release half-life of Drug is from about 0.1 hours to about 24 hours; and wherein the release half-life being measured in 0.05M phosphate buffer, 0.9% saline, pH 7.4, at 37° C.;

with the proviso that the conjugate of Formula I is not PHF-SA-Gly-CPT, PHF-(methyl)SA-Gly-CPT, PHF-(2,2-dimethyl)SA-Gly-CPT, PHF-(2-nonen-2-yl)SA-Gly-CPT, PHF-SA-Gly-Taxol, or PHF-SA-Gly-Illudin.

In another aspect, conjugates of the Formula II are described:

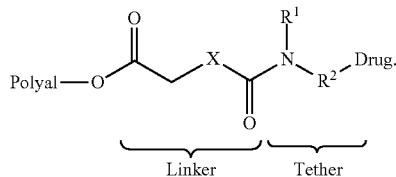

wherein

X is —$CH_2$—, —$OCH_2$—, or —$CH_2CH_2$—, wherein one or more of the $CH_2$ is optionally substituted;

$R_1$ is H or $CH_3$;

$R_2$ is —CH(Y)—C(O)—, wherein Y is one of the side chains of the naturally occurring amino acids, an aryl group, a heteroaryl group, a cycloalkyl, an alkyl group attached to both the N—$R_1$ and the Drug, or a heterocycle; or $R_1$ and $R_2$ when taken together with nitrogen to which they are attached form a ring;

Polyal is a polyacetal or polyketal;

Drug is any organic compound with a molecular weight of between about 200 daltons and 1000 daltons, capable of covalent attachment to the Tether;

wherein when Linker is a dicarboxylic acid with two atoms between the carbonyls and Tether contains a nitrogen with no reactive hydrogen, the release half-life of Drug is from about 10 h to more than about 300 h;

when Linker is a dicarboxylic acid with at least three atoms between the carbonyls and contains a heteroatom alpha to the carbonyl forming the ester, the release half-life is less than about 10 hours;

when Linker is a dicarboxylic acid with at least three atoms between the carbonyls with no heteroatom alpha to the carbonyl forming the ester, the release half-life is more than about 100 hours;

wherein when Linker is a dicarboxylic acid with two atoms between the carbonyls and Tether contains a nitrogen with a reactive hydrogen, the release half-life of Drug is from about 0.1 hours to about 20 hours;

wherein the release half-life being measured in 0.05M phosphate buffer, 0.9% saline, pH 7.4, at 37° C.;

with the proviso that the conjugate is not PHF-SA-Gly-CPT, PHF-(methyl)SA-Gly-CPT, PHF-(2,2-dimethyl)SA-Gly-CPT, PHF-(2-nonen-2-yl)SA-Gly-CPT, PHF-SA-Gly-Taxol, or PHF-SA-Gly-Illudin.

In some embodiments, the polyal is an acetal. In other embodiments, the polyal is a ketal. In some embodiments, the acetal is PHF. In some embodiments, $R_1$ is H. In other embodiments, $R_1$ is $CH_3$. In some embodiments, $R_2$ is —CH(Y)—C(O)—, wherein Y is one of the side chains of the naturally occurring amino acids. In some embodiments, $R_2$ is an aryl group. In some embodiments, $R_2$ is an heteroaryl group. In other embodiments, $R_2$ is an aliphatic ring. In some embodiments, $R_2$ is an aliphatic chain. In some embodiments, $R_2$ is a heterocyclic aliphatic ring. In some embodiments, $R_1$ and $R_2$ when taken together with nitrogen to which they are attached form a ring. In some embodiments, the ring which $R_1$ and $R_2$ form is a five-membered ring. In some embodiments, the ring which $R_1$ and $R_2$ form is a six-membered ring. In some embodiments, X is —$CH_2$—. In some embodiments, X is —$OCH_2$—. In some embodiments, X is —$CH_2CH_2$—. In some embodiments, X is optionally substituted with a $C_1$-$C_6$ alkyl group. In some embodiments, Tether is selected from the group consisting of an amino acid, a diamine, an aminoalcohol and an aminothiol. In some embodiments, Drug is a fumagillol analog. In some embodiments, Drug is a vinca alkaloid. In some embodiments, Drug is a non-natural camptothecin. In some embodiments, the non-natural camptothecin is SN38. In some embodiments, the conjugate is selected from the group consisting of wherein k ranges from 1-30, m ranges from 0-300, and n ranges from 100-750, and wherein the polyal comprises randomly distributed covalently bound monomer blocks shown in brackets; and pharmaceutically acceptable salts thereof.

In another aspect, conjugates of the Formula III are described:

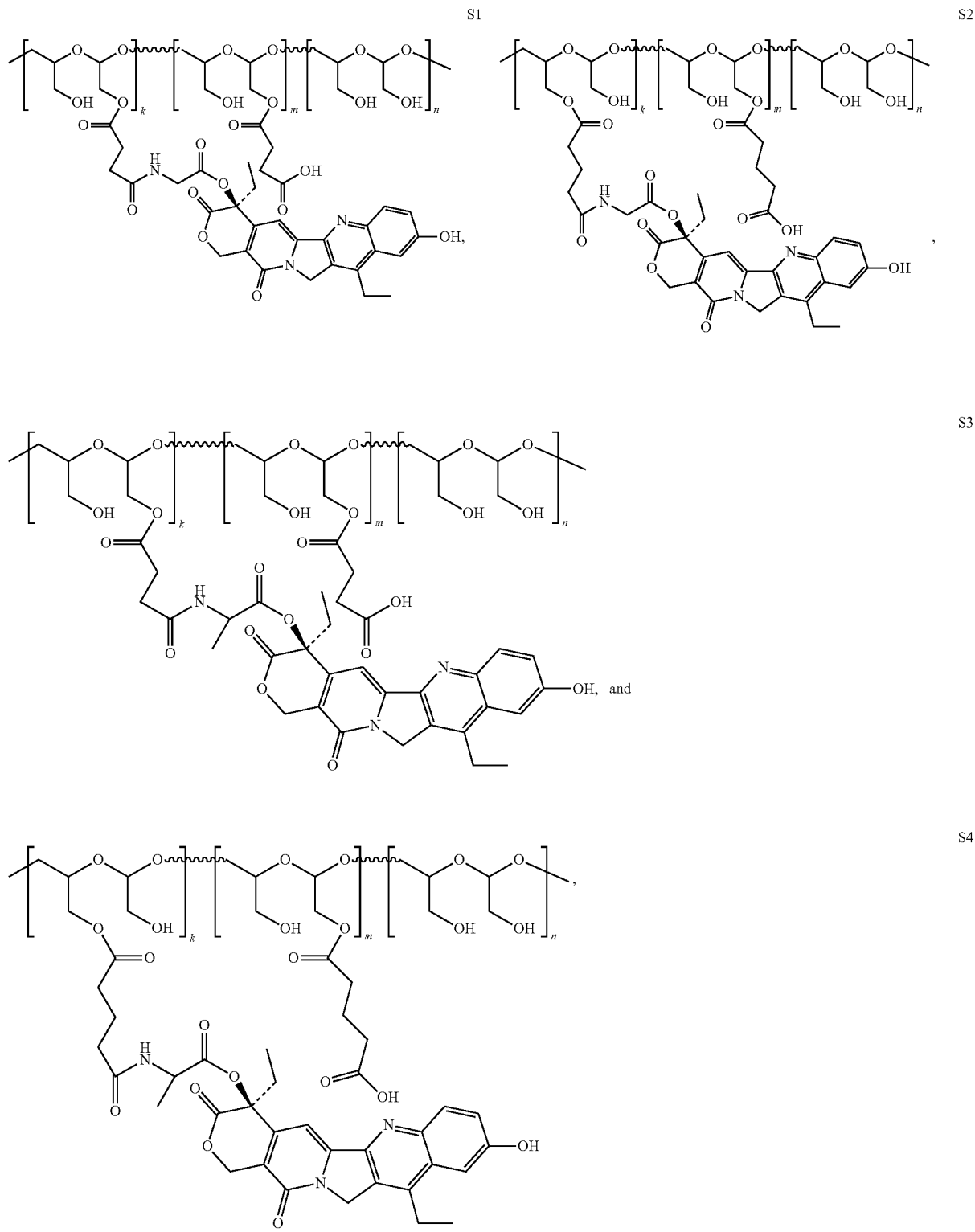

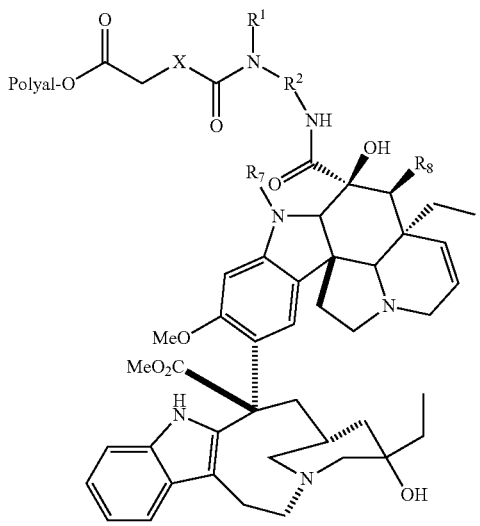

wherein
Polyal is a polyacetal or polyketal;
X is —CH$_2$—, —OCH$_2$—, or —CH$_2$CH$_2$—, wherein one or more of —CH$_2$— is optionally substituted;
R$_1$ is H or CH$_3$;
R$_2$ is —CH(Y)—C(O)—, wherein Y is one of the side chains of the naturally occurring amino acids, an aryl group, a heteroaryl group, a cycloalkyl, an alkyl group attached to both the N—R$_1$ and the —NHC(O)— of the vinca alkaloid derivative, or a heterocycle; or R$_1$ and R$_2$, when taken together with nitrogen to which they are attached, form a ring;
R$_7$ is —CH$_3$ or —CHO; and
R$_8$ is —OCOCH$_3$ or OH.

In another aspect, conjugates of the formula IV are described:

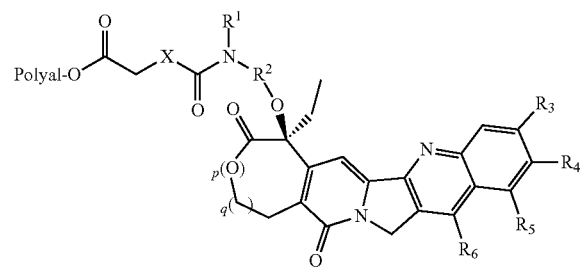

wherein
Polyal is a polyacetal or polyketal;
X is —CH$_2$—, —OCH$_2$—, or —CH$_2$CH$_2$—, wherein one or more of —CH$_2$— is optionally substituted;
R$_1$ is H or CH$_3$;
R$_2$ is —CH(Y)—C(O)—, wherein Y is one of the side chains of the naturally occurring amino acids, an aryl group, a heteroaryl group, a cycloalkyl, an alkyl group attached to both the N—R$_1$ and the —O— of the non-natural camptothecin derivative, or a heterocycle; or R$_1$ and R$_2$ when taken together with nitrogen to which they are attached form a ring;

R$_3$ is —H, —Cl, —F, —OH or alkyl; or R$_3$ and R$_4$, may be taken together to form a five- or six-membered ring;
R$_4$ is —H, —F, —OH, —CH$_3$, —CH=N—O-t-Butyl, —CH$_2$CH$_2$Si(CH$_3$)$_3$, or —Si((CH$_3$)$_2$)-t-Butyl;
R$_5$ is —CH$_2$—N(CH$_3$)$_2$, NH$_2$, or NO$_2$;
R$_6$ is ethyl, N-methyl piperidine, cycloalkyl, —CH$_2$CH$_2$NHCH(CH$_3$)$_2$, or —N-4-methylcyclohexylamine;
or R$_5$ and R$_6$, may be taken together to form a six-membered optionally substituted ring;
p is 0 or 1; and
q is 0 or 1;
with the proviso that the conjugate is not PHF-SA-Gly-CPT, PHF-(methyl)SA-Gly-CPT, PHF-(2,2-dimethyl)SA-Gly-CPT, or PHF-(2-nonen-2-yl)SA-Gly-CPT.

In another aspect, a method of identifying a Polyal-Drug conjugate having a drug release half-life of between about 0.1 hours and greater than 300 hours, as measured in phosphate buffered saline (PBS) at 37° C. is described, the method comprising: selecting a dicarboxylic acid Linker; obtaining a conjugate with said Linker, the conjugate comprising Polyal, Drug, and said Linker; and determining the release half-life of Drug from the conjugate.

In another aspect, pharmaceutical compositions comprising a polyal-non-natural camptothecin conjugate or a pharmaceutically acceptable salt of a polyal-non-natural camptothecin conjugate and a pharmaceutically acceptable carrier are provided.

In another aspect, methods of treating cancer, comprising administering to a subject in need thereof a polyal-non-natural camptothecin conjugate or a pharmaceutically acceptable salt of a polyal-non-natural camptothecin conjugate in an amount effective to treat the cancer are described.

In some embodiments, the polyal-non-natural camptothecin useful for treating cancer is a PHF-non-natural camptothecin conjugate. In another embodiment, the PHF-non-natural camptothecin conjugate useful for treating cancer is PHF-SN38 conjugate.

In some embodiments, the cancer is selected from the group consisting of: anal, astrocytoma, leukemia, lymphoma, head and neck, liver, testicular, cervical, sarcoma, hemangioma, esophageal, eye, laryngeal, mouth, mesothelioma, skin, myeloma, oral, rectal, throat, bladder, breast, uterus, ovary, prostate, lung, colon, pancreas, renal, and gastric.

In another aspect, pharmaceutical compositions comprising a polyal-vinca alkaloid conjugate or a pharmaceutically acceptable salt of a polyal-vinca alkaloid conjugate and a pharmaceutically acceptable carrier are provided.

In another aspect, methods of treating cancer, comprising administering to a subject in need thereof a polyal-vinca alkaloid conjugate or a pharmaceutically acceptable salt of a polyal-vinca alkaloid conjugate in an amount effective to treat the cancer are described.

In some embodiments, the polyal-vinca alkaloid conjugate useful for treating cancer is a PHF-vinca alkaloid conjugate.

In some embodiments, the cancer is selected from the group consisting of: anal, astrocytoma, leukemia, lymphoma, head and neck, liver, testicular, cervical, sarcoma, hemangioma, esophageal, eye, laryngeal, mouth, mesothelioma, skin, myeloma, oral, rectal, throat, bladder, breast, uterus, ovary, prostate, lung, colon, pancreas, renal, and gastric.

DETAILED DESCRIPTION

Definitions

Figure 1:
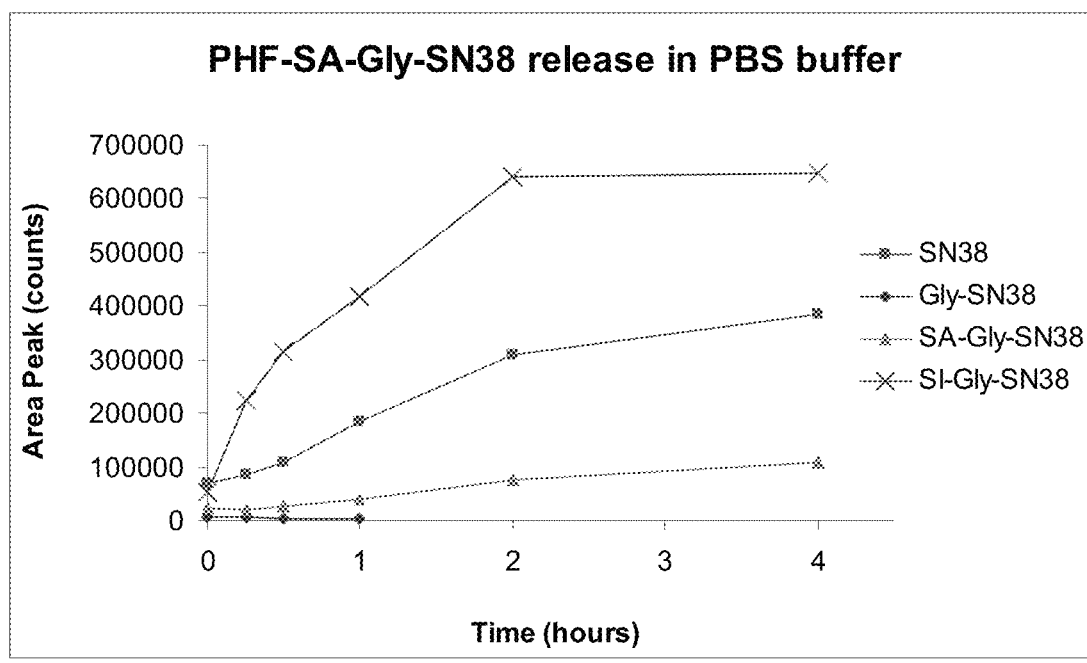
FIG. 1 depicts the release of PHF-SA-Gly-SN38 in PBS buffer.
Figure 2:
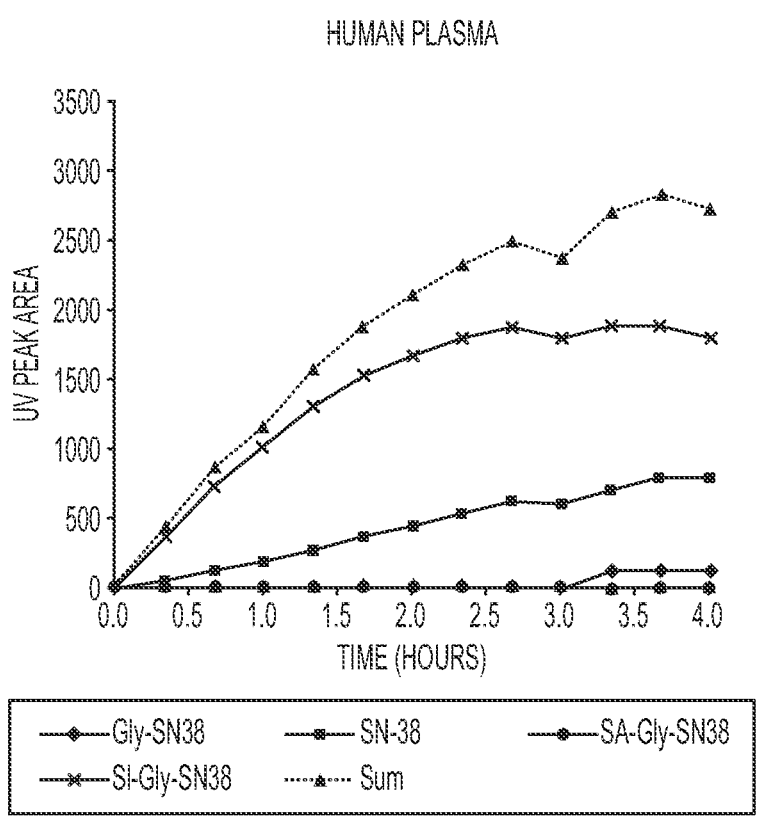
FIG. 2 depicts the release of PHF-SA-Gly-SN38 in human plasma.
Figure 3:
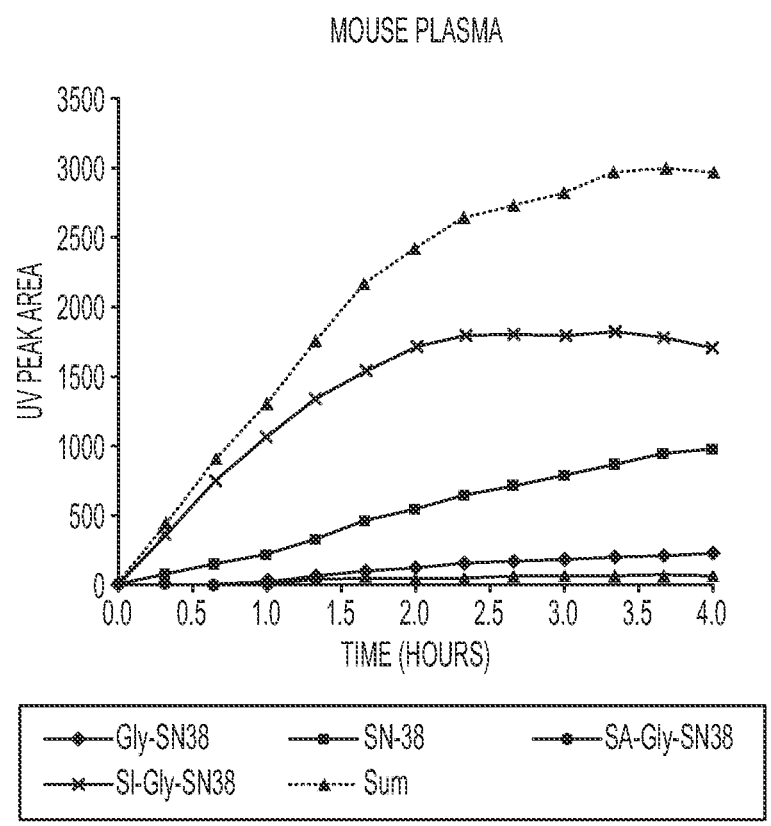
FIG. 3 depicts the release of PHF-SA-Gly-SN38 in mouse plasma.
Figure 4:
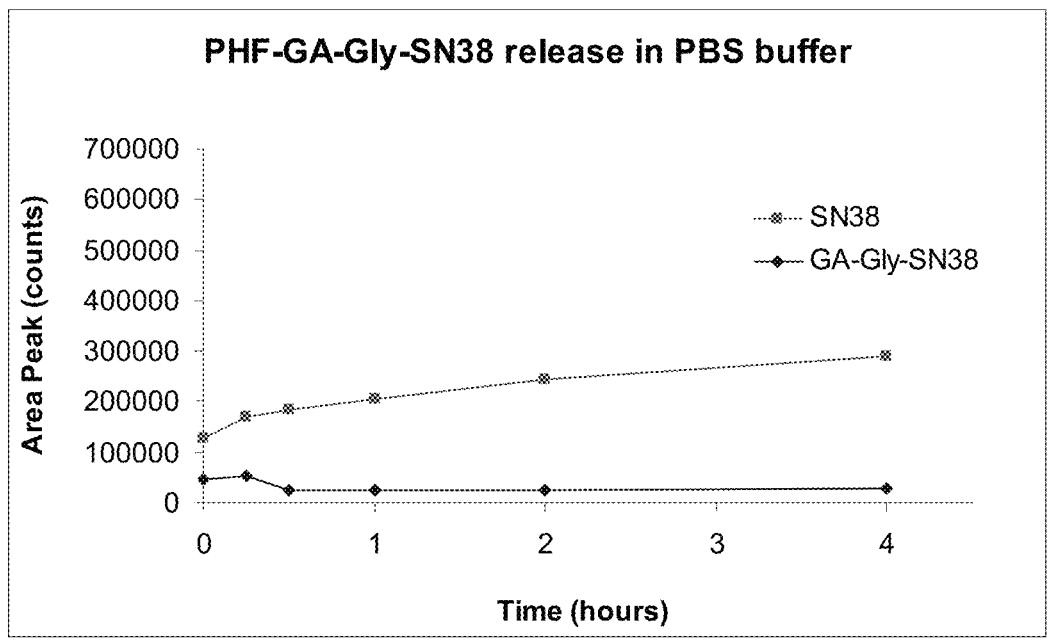
FIG. 4 depicts the release of PHF-GA-Gly-SN38 in PBS buffer.
Figure 5:
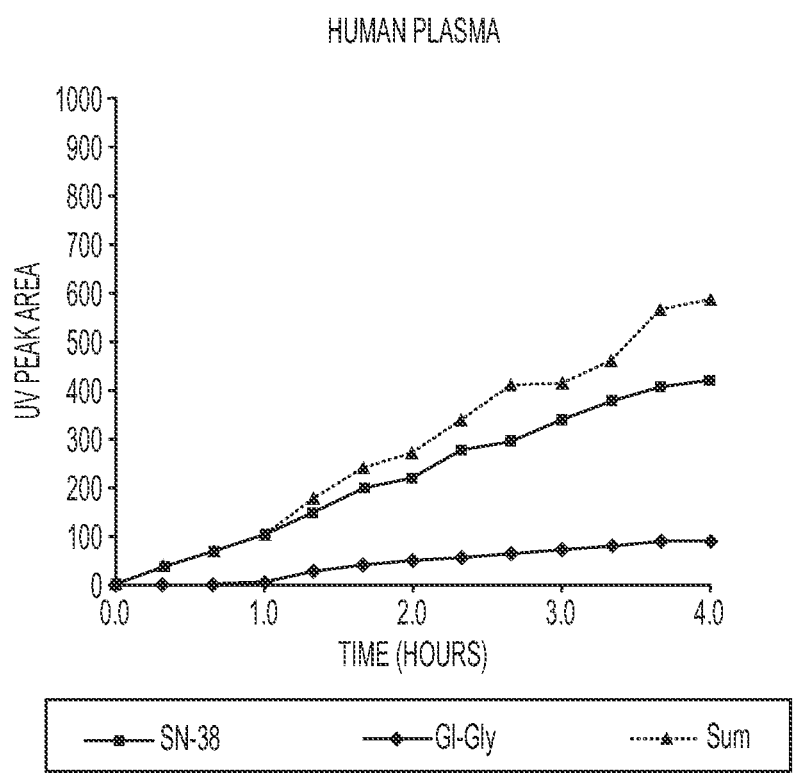
FIG. 5 depicts the release of PHF-GA-Gly-SN38 in human plasma.
Figure 6:
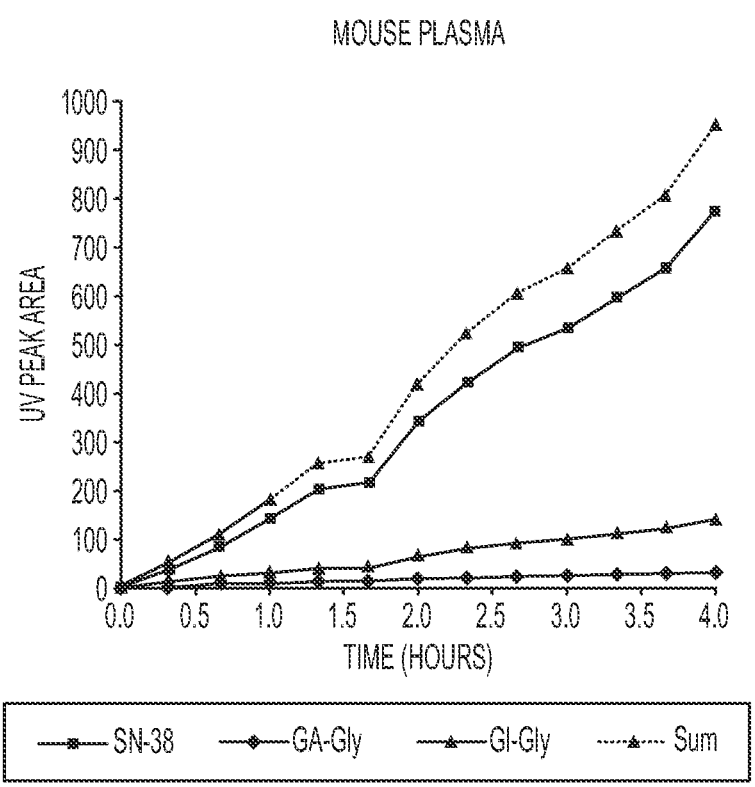
FIG. 6 depicts the release of PHF-GA-Gly-SN38 in mouse plasma.
Figure 7:
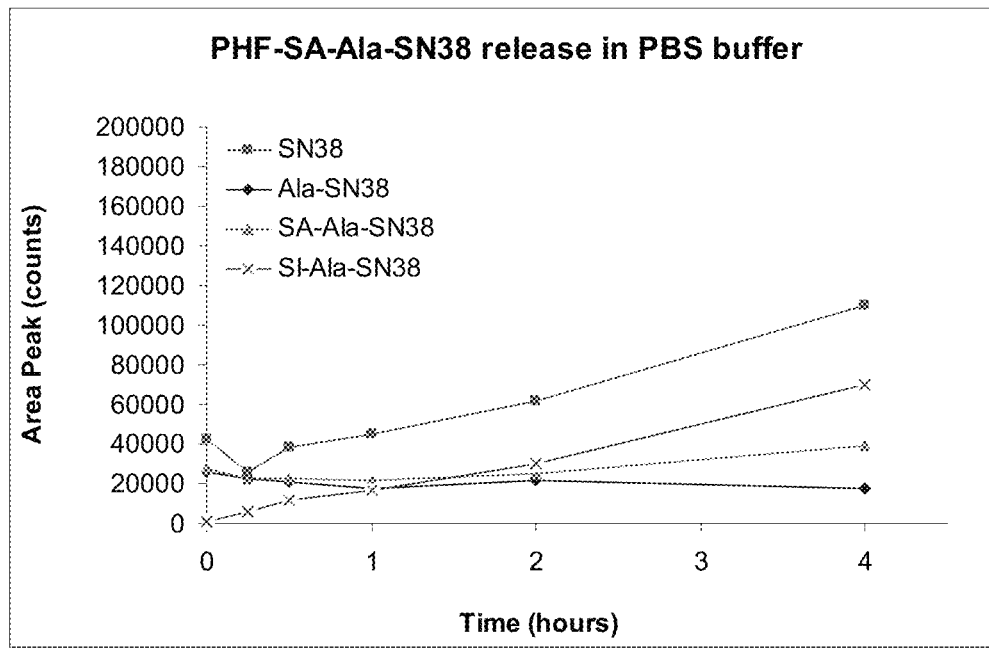
FIG. 7 depicts the release of PHF-SA-Ala-SN38 in PBS buffer.
Figure 8:
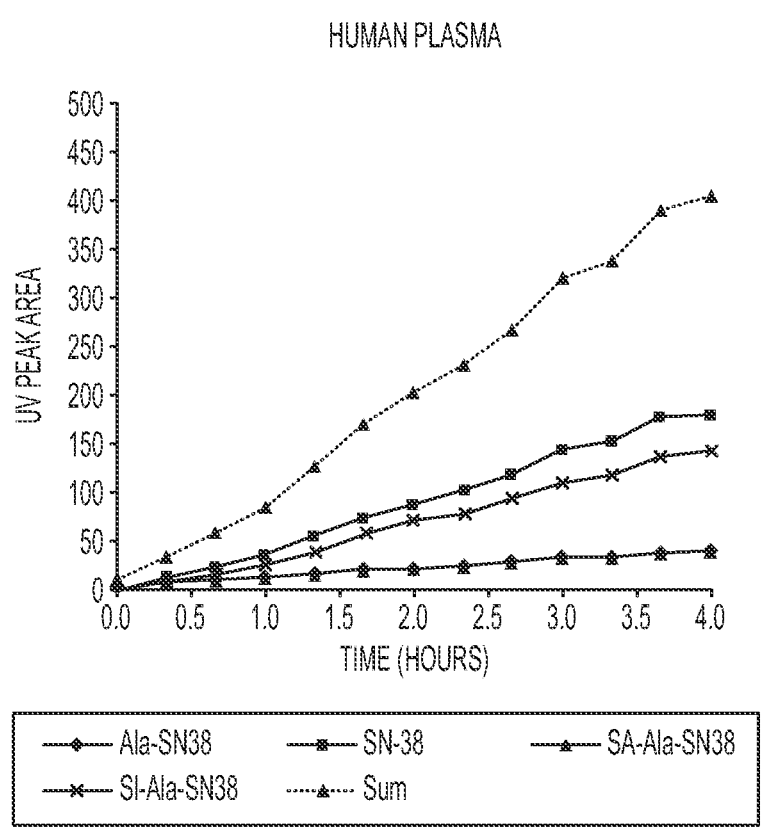
FIG. 8 depicts the release of PHF-SA-Ala-SN38 in human plasma.
Figure 9:
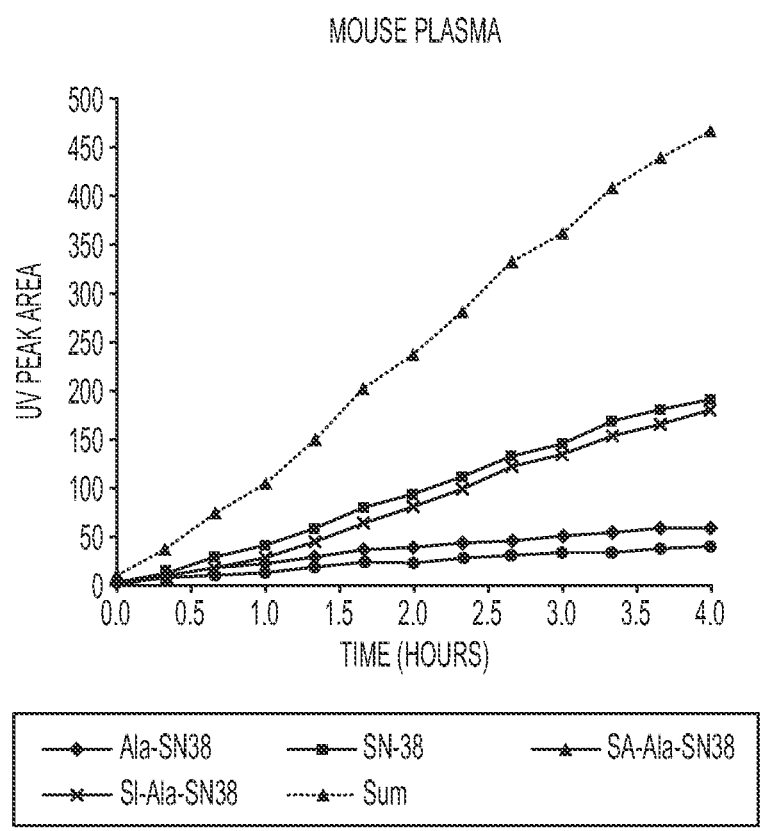
FIG. 9 depicts the release of PHF-SA-Ala-SN38 in mouse plasma.
Figure 10:
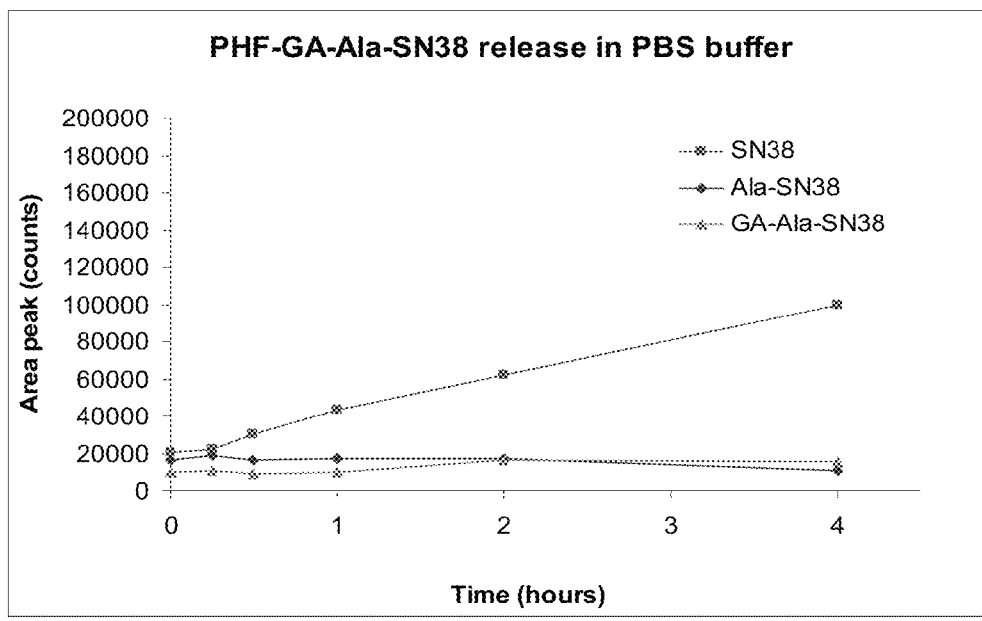
FIG. 10 depicts the release of PHF-GA-Ala-SN38 in PBS buffer.
Figure 11:
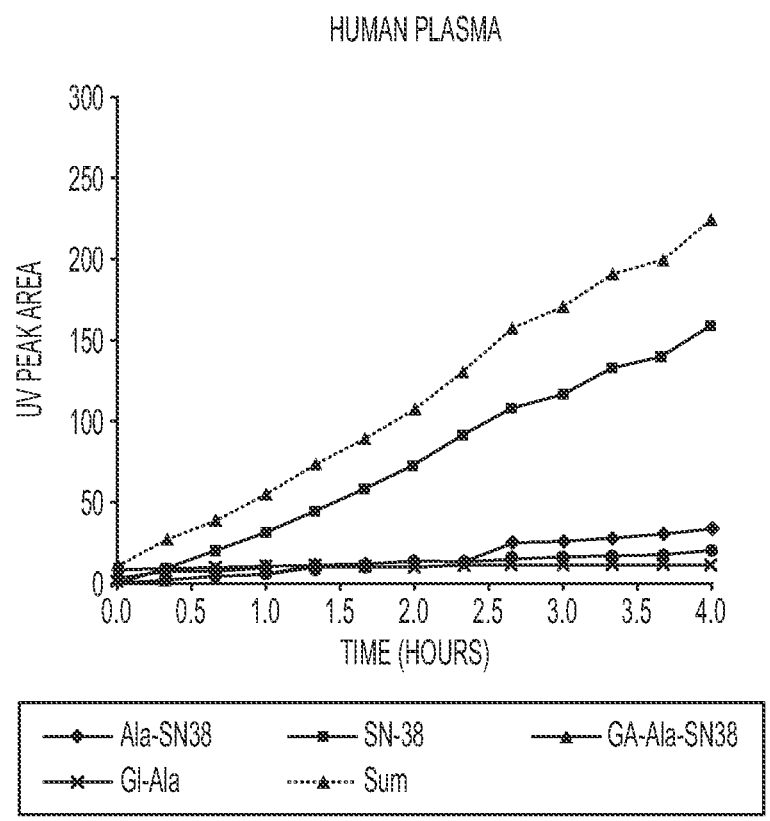
FIG. 11 depicts the release of PHF-GA-Ala-SN38 in human plasma.
Figure 12:
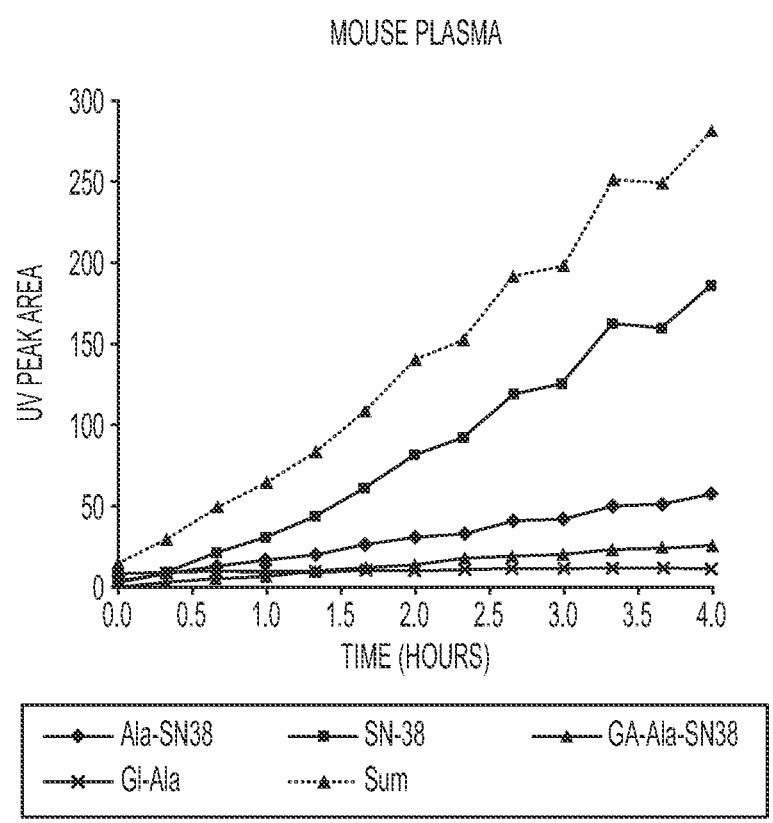
FIG. 12 depicts the release of PHF-GA-Ala-SN38 in mouse plasma.

The following definitions are used in connection with the Polyal-Drug conjugates comprising variable rate-releasing linkers:

"Alkyl" refers to a hydrocarbon chain that may be a straight chain or branched chain. The chain my contain an indicated number of carbon atoms. For example, $C_1$-$C_6$ indicates that the group may have from 1 to 6 (inclusive) carbon atoms in it.

"Aryl" refers to cyclic aromatic carbon ring systems containing from 6 to 18 carbons. Examples of an aryl group include, but are not limited to, phenyl, naphthyl, anthracenyl, tetracenyl, and phenanthrenyl. An aryl group can be unsubstituted or substituted with one or more of the following groups: H, halogen, CN, OH, aryl, arylalkyl, heteroaryl, heteroarylalkyl, $C_{1-6}$ alkyl, $C_{2-6}$ alkenyl, $C_{2-6}$ alkynyl, $C_{1-3}$ fluorinated-alkyl, $C_{3-6}$ cycloalkyl, $C_{3-6}$cycloalkyl-$C_{1-3}$alkyl, $NO_2$, $NH_2$, $NHC_{1-6}$ alkyl, $N(C_{1-6}$ alkyl$)_2$, $NHC_{3-6}$ cycloalkyl, $N(C_{3-6}$ cycloalkyl$)_2$, $NHC(O)C_{1-6}$ alkyl, $NHC(O)C_{3-6}$ cycloalkyl, $NHC(O)NHC_{1-6}$ alkyl, $NHC(O)NHC_{3-6}$ cycloalkyl, $SO_2NH_2$, $SO_2NHC_{1-6}$ alkyl, $SO_2NHC_{3-6}$ cycloalkyl, $SO_2N(C_{1-6}$ alkyl$)_2$, $SO_2N(C_{3-6}$ cycloalkyl$)_2$, $NHSO_2C_{1-6}$ alkyl, $NHSO_2C_{3-6}$ cycloalkyl, $CO_2C_{1-6}$ alkyl, $CO_2C_{3-6}$ cycloalkyl, $CONHC_{1-6}$ alkyl, $CONHC_{3-6}$ cycloalkyl, $CON(C_{1-6}$ alkyl$)_2$, $CON(C_{3-6}$ cycloalkyl$)_2$OH, $OC_{1-3}$ alkyl, $C_{1-3}$ fluorinated-alkyl, $OC_{3-6}$ cycloalkyl, $OC_{3-6}$ cycloalkyl-$C_{1-3}$ alkyl, SH, $SO_xC_{1-3}$ alkyl, $C_{3-6}$ cycloalkyl, or $SO_xC_{3-6}$ cycloalkyl-$C_{1-3}$ alkyl, where x is 0, 1, or 2.

"Heteroaryl" refers to mono and bicyclic aromatic groups of 4 to 10 atoms containing at least one heteroatom. Heteroatom as used in the term heteroaryl refers to oxygen, sulfur and nitrogen. Examples of monocyclic heteroaryls include, but are not limited to, oxazinyl, thiazinyl, diazinyl, triazinyl, tetrazinyl, imidazolyl, tetrazolyl, isoxazolyl, furanyl, furazanyl, oxazolyl, thiazolyl, thiophenyl, pyrazolyl, triazolyl, and pyrimidinyl. Examples of bicyclic heteroaryls include but are not limited to, benzimidazolyl, indolyl, isoquinolinyl, indazolyl, quinolinyl, quinazolinyl, purinyl, benzisoxazolyl, benzoxazolyl, benzthiazolyl, benzodiazolyl, benzotriazolyl, isoindolyl and indazolyl. A heteroaryl group can be unsubstituted or substituted with one or more of the following groups: H, halogen, CN, OH, aryl, arylalkyl, heteroaryl, heteroarylalkyl, $C_{1-6}$ alkyl, $C_{2-6}$ alkenyl, $C_{2-6}$ alkynyl, $C_{1-3}$ fluorinated-alkyl, $C_{3-6}$ cycloalkyl, $C_{3-6}$cycloalkyl-$C_{1-3}$alkyl, $NO_2$, $NH_2$, $NHC_{1-6}$ alkyl, $N(C_{1-6}$ alkyl$)_2$, $NHC_{3-6}$ cycloalkyl, $N(C_{3-6}$ cycloalkyl$)_2$, $NHC(O)C_{1-6}$ alkyl, $NHC(O)C_{3-6}$ cycloalkyl, $NHC(O)NHC_{1-6}$ alkyl, $NHC(O)NHC_{3-6}$ cycloalkyl, $SO_2NH_2$, $SO_2NHC_{1-6}$ alkyl, $SO_2NHC_{3-6}$ cycloalkyl, $SO_2N(C_{1-6}$ alkyl$)_2$, $SO_2N(C_{3-6}$ cycloalkyl$)_2$, $NHSO_2C_{1-6}$ alkyl, $NHSO_2C_{3-6}$ cycloalkyl, $CO_2C_{1-6}$ alkyl, $CO_2C_{3-6}$ cycloalkyl, $CONHC_{1-6}$ alkyl, $CONHC_{3-6}$ cycloalkyl, $CON(C_{1-6}$ alkyl$)_2$, $CON(C_{3-6}$ cycloalkyl$)_2$OH, $OC_{1-3}$ alkyl, $C_{1-3}$ fluorinated-alkyl, $OC_{3-6}$ cycloalkyl, $OC_{3-6}$ cycloalkyl-$C_{1-3}$ alkyl, SH, $SO_xC_{1-3}$ alkyl, $C_{3-6}$ cycloalkyl, or $SO_xC_{3-6}$ cycloalkyl-$C_{1-3}$ alkyl, where x is 0, 1, or 2.

"$C_1$-$C_6$ alkyl" refers to a straight or branched chain saturated hydrocarbon containing 1-6 carbon atoms. Examples of a $C_1$-$C_6$ alkyl group include, but are not limited to, methyl, ethyl, propyl, isopropyl, n-pentyl, isopentyl, neopentyl, and hexyl.

"$C_1$-$C_6$ alkoxy" refers to a straight or branched chain saturated or unsaturated hydrocarbon containing 1-6 carbon atoms and at least one oxygen atom. Examples of a $C_1$-$C_6$-alkoxy include, but are not limited to, methoxy, ethoxy, isopropoxy, butoxy, n-pentoxy, isopentoxy, neopentoxy, and hexoxy.

"Cycloalkyl" refers to a cyclic saturated hydrocarbon. Examples of a cycloalkyl group include, but are not limited to, cyclopropane, cyclobutane, cyclopentane, cyclohexane, cycloheptane, and cyclooctane.

"Heterocycle" refers to a cyclic saturated hydrocarbon wherein at least one of the carbons is replaced by N, S, or O. Examples of heterocycle include, but are not limited to, azetidine, oxetane, thietane, azolidine, pyrrolidine, tetrahydrofuran, tetrahydrothiophene, imidazolidine, oxazolidine, thiazolidine, morpholine, piperidine, tetrahydropyran, thiane, piperazine, oxazine, and dioxane.

"Halogen" refers to an atom of fluorine, chlorine, bromine, or iodine.

"Cyclized imide" and "cyclic-imide" refer to either saturated or unsaturated cyclic or heterocyclic compounds that contain the imide functional group which consists of two carbonyl groups bound to a nitrogen atom. Cyclic-imides can be further substituted with other functional groups. Examples of a cyclic-imide include, but are not limited to, piperidyl-2,6-dione, morpholyl-3,5-dione, and pyrrolidyl-2,5-dione.

The term "optionally substituted $CH_2$" when used herein means that one or both hydrogen atoms may be substituted with one or more of the following groups: OH, halogen, CN, $C_1$-$C_6$ alkyl, $C_2$-$C_6$ alkenyl, $C_2$-$C_6$ alkynyl, $C_1$-$C_6$ alkoxy, $C_1$-$C_3$ fluorinated alkyl, $NO_2$, $NH_2$, $NHC_1$-$C_6$ alkyl, $N(C_1$-$C_6$ alkyl$)_2$, $NHC(O)C_1$-$C_6$ alkyl, $NHC(O)NHC_1$-$C_6$ alkyl, $SO_2NH_2$, $SO_2NHC_1$-$C_6$ alkyl, $SO_2N(C_1$-$C_6$ alkyl$)_2$, $NHSO_2C_1$-$C_6$ alkyl, $C(O)OC_1$-$C_6$ alkyl, $CONHC_1$-$C_6$ alkyl, $CON(C_1$-$C_6$ alkyl$)_2$, $C_1$-$C_6$ alkyl, or both hydrogen atoms may be substituted and the substituted groups when taken together with the carbon to which they are attached, form a cycloalkyl or heterocycloalkyl, each optionally substituted with $C_1$-$C_6$ alkyl, $C_2$-$C_6$ alkenyl, $C_2$-$C_6$ alkynyl, $C_1$-$C_6$ alkoxy, $CO_2C_1$-$C_6$ alkyl, CN, OH, cycloalkyl, $CONH_2$, aryl, heteroaryl, COaryl, or trifluoroacetyl.

The term "pharmaceutically acceptable salts" include, e.g., water-soluble and water-insoluble salts, such as the acetate, amsonate (4,4-diaminostilbene-2,2-disulfonate), benzenesulfonate, benzoate, bicarbonate, bisulfate, bitartrate, borate, bromide, butyrate, calcium edetate, camsylate, carbonate, chloride, citrate, clavulariate, dihydrochloride, edetate, edisylate, estolate, esylate, fumarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosaliculate, suramate, tannate, tartrate, teoclate, tosylate, triethiodide, and valerate salts.

The term "PHF" means [poly-(1-hydroxymethylethylene hydroxy-methyl formal)].

The term "non-natural camptothecin" means a compound based on the structure of the natural product camptothecin (CPT). Non-limiting examples of non-natural camptothecins include topotecan, SN-38, 9-aminocamptothecin, rubitecan, gimatecan, karenitecin, silatecan, lurtotecan, exatecan, diflomotecan, belotecan, and S39625.

The term "fumagillol analog" means any fumagillin core structure, including fumagillamine, that inhibits the ability of MetAP-2 to remove $NH_2$-terminal methionines from proteins as described in Rodeschini et al., *J. Org. Chem.*, 69, 357-373, 2004 and Liu, et al., *Science* 282, 1324-1327, 1998. Nonlimiting examples of "fumagillol analogs" are disclosed in *J. Org. Chem.*, 69, 357, 2004; *J. Org. Chem.*, 70, 6870, 2005; European Patent Application 0 354 787; *J. Med. Chem.*, 49, 5645, 2006; *Bioorg. Med. Chem.*, 11, 5051, 2003; *Bioorg. Med. Chem.*, 14, 91, 2004; *Tet. Lett.* 40, 4797, 1999; WO99/61432; U.S. Pat. Nos. 6,603,812; 5,789,405; 5,767,293; 6,566,541; and 6,207,704.

The term "polyal" means a polymer having at least one acetal or ketal oxygen atom in each monomer unit positioned within the main chain. Examples of polyals can be found in U.S. Pat. Nos. 5,811,510, 5,863,990, 5,958,398 and international application PCT/US2004/029130 which are incorporated herein by reference in their entirety. In certain embodiments, biodegradable biocompatible polymer carriers, useful for preparation of polymer conjugates described herein, are naturally occurring polysaccharides, glycopolysaccharides, and synthetic polymers of polyglycoside, polyacetal, polyamide, polyether, and polyester origin and products of their oxidation, functionalization, modification, cross-linking, and conjugation. When the monomer units of a polyal are depicted herein the two free hydroxyls therein are equally reactive during derivatization and therefore either hydroxyl may be actually derivatized not just the one depicted.

The following abbreviations are used herein and have the indicated definitions: EDC (1-ethyl-3-(3-dimethylaminopropyl)carbodiimide hydrochloride), ACN (acetonitrile), CPT (camptothecin), Gly (glycine), Ala (alanine), DMAP (dimethylamino pyridine), PHF-GA (poly(1-hydroxymethylethylene hydroxymethyl-formal) conjugated to glutaric acid), PHF-SA (poly(1-hydroxymethylethylene hydroxymethyl-formal) conjugated to succinic acid), DMF (dimethyl formamide), HPLC (high pressure liquid chromatography), TBDPS (tert-butyldiphenylsilyl), TBAF (Tetra-n-butylammonium fluoride), FBS (fetal bovine serum), PBS (phosphate buffered saline (0.05M phosphate, 0.9% saline)), DCM (dichloromethane), DIPC (diisopropylcarbodiimide), DI (deionized), RP (reverse-phase), SEC (size exclusion), r.t. (room temperature).

Variable Rate-Releasing Linkers

In has been unexpectedly discovered that amidoester linkages utilized to link polymeric carriers with drugs are capable of releasing the drugs or prodrugs under physiological conditions, in a pH-dependent manner. Such linkages comprise a dicarboxylic acid attached to a hydroxyl moiety of a polyhydroxylated polymer carrier such as, for example, a polyal, via an ester bond, and an amino group containing a bifunctional tether via an amide bond. Tether can provide for functional modification of Drug in order to introduce the amino group which is capable of forming the amide with the dicarboxylic acid moiety in the process of drug conjugation.

In one aspect of this disclosure, conjugates of the Formula I are described

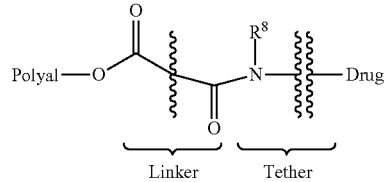

wherein
Polyal is a polyacetal or polyketal; C-b1
Linker is a dicarboxylic acid moiety containing two or more atoms between the carbonyls; C-b3
Tether is a bifunctional organic moiety comprising a secondary or tertiary amine;
$R_a$ is H, alkyl, or together with a $CH_2$ of the backbone of the Tether forms a five- or six-membered ring; and C-b2
Drug is any organic compound with a molecular weight of between about 200 daltons and 1000 daltons, capable of covalent attachment to the Tether;
wherein
  when Linker is a dicarboxylic acid with two atoms between the carbonyls and Tether contains a nitrogen with no reactive hydrogen, the release half-life of Drug is from about 10 h to more than about 300 h;
  when Linker is a dicarboxylic acid with at least three atoms between the carbonyls and contains a heteroatom alpha to the carbonyl forming the ester, the release half-life is less than about 10 hours;
  when Linker is a dicarboxylic acid with at least three atoms between the carbonyls with no heteroatom alpha to the carbonyl forming the ester, the release half-life is more than about 100 hours;
wherein
  when Linker is a dicarboxylic acid with two atoms between the carbonyls and Tether contains a nitrogen with a reactive hydrogen the release half-life of Drug is from about 0.1 hours to about 24 hours;
wherein
  the release half-life being measured in 0.05M phosphate buffer, 0.9% saline, pH 7.4, at 37° C.;
with the proviso that the compound is not PHF-SA-Gly-CPT, PHF-(methyl)SA-Gly-CPT, PHF-(2,2-dimethyl)SA-Gly-CPT, PHF-(2-nonen-2-yl)SA-Gly-CPT, PHF-SA-Gly-Taxol, or PHF-SA-Gly-Illudin.

In another aspect, conjugates of the Formula II are described:

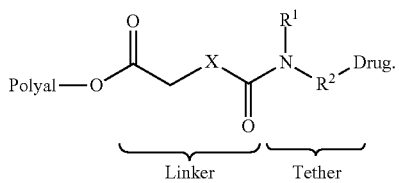

wherein

X is —CH$_2$—, —OCH$_2$—, or —CH$_2$CH$_2$—, wherein one or more of the CH$_2$ is optionally substituted;

R$_1$ is H or CH$_3$;

R$_2$ is —CH(Y)—C(O)—, wherein Y is one of the side chains of the naturally occurring amino acids, an aryl group, a heteroaryl group, a cycloalkyl, an alkyl group attached to both the N—R$_1$ and the Drug, or a heterocycle; or R$_1$ and R$_2$ when taken together with nitrogen to which they are attached form a ring;

Polyal is a polyacetal or polyketal; and

Drug is any organic compound with a molecular weight of between about 200 daltons and 1000 daltons, capable of covalent attachment to the Tether;

wherein when Linker is a dicarboxylic acid with two atoms between the carbonyls and Tether contains a nitrogen with no reactive hydrogen, the release half-life of Drug is from about 10 h to more than about 300 h;

when Linker is a dicarboxylic acid with at least three atoms between the carbonyls and contains a heteroatom alpha to the carbonyl forming the ester, the release half-life is less than about 10 hours;

when Linker is a dicarboxylic acid with at least three atoms between the carbonyls with no heteroatom alpha to the carbonyl forming the ester, the release half-life is more than about 100 hours;

wherein when Linker is a dicarboxylic acid with two atoms between the carbonyls and Tether contains a nitrogen with a reactive hydrogen the release half-life of Drug is from about 0.1 hours to about 24 hours;

wherein the release half-life being measured in 0.05M phosphate buffer, 0.9% saline, pH 7.4, at 37° C.;

with the proviso that the compound is not PHF-SA-Gly-CPT, PHF-(methyl)SA-Gly-CPT, PHF-(2,2-dimethyl)SA-Gly-CPT, PHF-(2-nonen-2-yl)SA-Gly-CPT, PHF-SA-Gly-Taxol, or PHF-SA-Gly-Illudin.

In some embodiments, polyal is an acetal.
In some embodiments, polyal is a ketal.
In some embodiments, the acetal is PHF.
In some embodiments, R$_1$ is H.
In some embodiments, R$_1$ is CH$_3$.
In some embodiments, R$_2$ is —CH(Y)—C(O)—, wherein Y is one of the side chains of the naturally occurring amino acids.
In some embodiments, R$_2$ is an aromatic group.
In some embodiments, R$_2$ is a heteroaryl group.
In some embodiments, R$_2$ is an aliphatic group.
In some embodiments, R$_2$ is an aliphatic chain.
In some embodiments, R$_2$ is a heterocyclic aliphatic ring.
In some embodiments, R$_1$ and R$_2$, when taken together with nitrogen to which they are attached, form a ring.
In some embodiments, the ring which R$_1$ and R$_2$ form is a five-membered ring.

In some embodiments, the ring which R$_1$ and R$_2$ form is a six-membered ring.
In some embodiments, X is —CH$_2$—.
In some embodiments, X is —OCH$_2$—.
In some embodiments, X is —CH$_2$CH$_2$—.
In some embodiments, X is optionally substituted with a C$_1$-C$_6$ alkyl group.
In some embodiments, the bifunctional tether —(N—R$_2$)— is an amino acid, a diamine, an aminoalcohol or an aminothiol.
In some embodiments, Drug is fumagillol.
In some embodiments, Drug is a vinca alkaloid.
In some embodiments, Drug is a non-natural camptothecin.

In another aspect, a method of identifying a Polyal-Drug conjugate having a drug release half-life of between about 0.1 hours and greater than 300 hours as measured in PBS buffer at 37° C. is described, the method comprising: selecting a dicarboxylic acid Linker; obtaining a conjugate with said Linker, the conjugate comprising Polyal, Drug, and said Linker; and determining the release half-life of Drug from the conjugate.

It has been discovered that by judicious choice of Linker and Tether, Drug can be released from the Polyal-Drug conjugate via at least two independent pathways, either (A) intramolecular rearrangement of the amidoester linkage resulting in cleavage of the Polyal-ester bond accompanied by formation of a cyclic imide at the Drug site; or (B) hydrolysis of the ester bond between Polyal and the amidoester Linker resulting in release of Drug-amidoacid derivative (see Scheme 1).

Scheme 1.

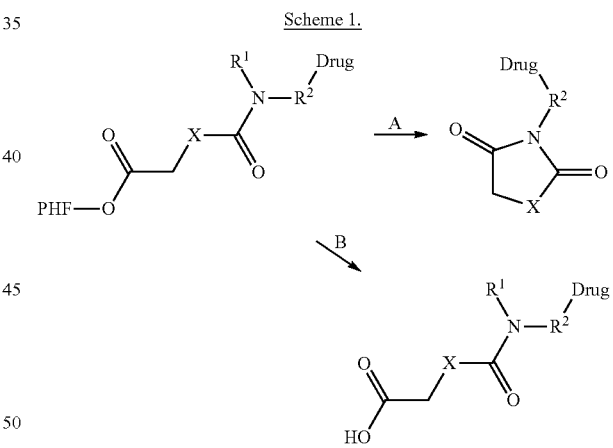

When R$_1$ is H and X is CH$_2$, the cleavage of Drug from Polyal proceeds through process A. Under most other conditions, the ester portion of the linkage undergoes hydrolysis.

The stability of the amidoester linkages is pH-dependent with an increase in the pH of an aqueous solution accelerating both intramolecular rearrangement of the amidoester and ester bond hydrolysis of the Polyal-Drug conjugate. When the Polyal-Drug conjugate is evaluated at physiological conditions, i.e., 0.05M phosphate pH 7.4 buffered saline, 0.9% NaCl (PBS), at 37° C., the predominant mechanism (process A (intramolecular) or process B (intermolecular hydrolysis)) and the rate of release of Drug from Polyal can be influenced by structural characteristics of the amidoester based on careful selection of the dicarboxylic acid Linker and the amine-containing Tether attached to Drug.

Intramolecular Release (Process A)

For Linkers with two atoms between the carbonyl groups of the dicarboxylic acid linker (e.g. succinic acid derivatives (SA)) the release product composition and the rate of release may be effectively controlled by a combination of steric and electronic effects in both the dicarboxylic acid Linker and the amine-containing Tether. For succinic acid derivatives, the release half-life of Drug (in PBS buffer, pH 7.4, at 37° C.) can be adjusted to between from about 0.1 h to greater than 100 h. The release product composition can vary from predominantly the cyclic succinimide drug derivatives which result from the intramolecular release process, to succinic acid amide drug derivatives, which result from an intermolecular release process. Both of these processes depend upon the selection of the amine-containing Tether employed.

For example, when the release of succinimide derivatives is desired (i.e. intramolecular release process A) the release half-life of Polyal-Drug conjugate can be adjusted by altering the steric effect of the $R_2$ group. Increasing this steric effect hinders the intramolecular nucleophilic attack of the nitrogen on the carbonyl of the ester end of the linkage. Conjugates V1, V2, and V3 (Scheme 2) for which the amine-containing tether is glycine, β-alanine and alanine respectively, the increase in the steric hindrance of Tether at $R_2$ (glycine<β-alanine<alanine) results in an increase of the release half-life of Drug from 3.4 hours to 17 hours and 19 hours, respectively, when tested in PBS, pH 7.4 at 37° C.

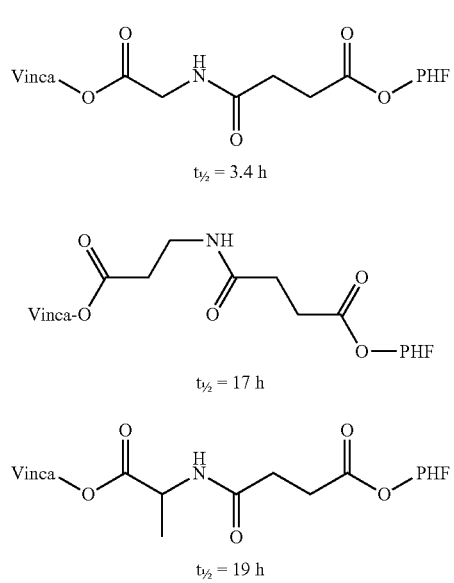

Scheme 2

The release half-life can be attenuated also by the electronic properties of the $R_2$ moiety. For example, when $R_2$ is an aromatic ring bound to the nitrogen, substituents on the aromatic ring that influence the electronic density on the nitrogen affect the rate of nucleophilic attack of the nitrogen on the carbonyl.

Intermolecular Release (Process B)

When the ester portion of the amidoester linkage is targeted as the primary conjugate drug release product (i.e. by intermolecular release mechanism), the release half-life of Drug can be adjusted by employing Linkers with differing numbers of atoms between the two carbonyls of the dicarboxylic acid, the electronic influence alpha to the carbonyl forming the ester (e.g. glutaric acid (GA) and oxaglutaric acid (OGA)), and Linker/Tether combinations (e.g. succinic acid-Tether derivatives).

For succinic acid derivatives, the release half-life of the corresponding succinic acid amide derivatives from the conjugates can be attenuated by changing the amine-containing Tethers. Use of secondary amine tethers (i.e. amines in which the nitrogen does not have a reactive hydrogen directly attached to the nitrogen) can be used to eliminate the possibility of succinimide formation (i.e. intramolecular release process), and the steric hindrance at $R_2$ will control the release half-life of Drug via the intermolecular mechanism. For example, the Tether sarcosine along with succinic acid provides a release half-life of Drug of 81 hours for the conjugate V8, while conjugate V13, with the more hindered Tether proline, instead of sarcosine, under the same conditions, (PBS, pH 7.4, 37° C.) releases Drug with a half-life of 375 hours.

Linkers with three or more atoms in the carbon or heteroatom chain connecting the carboxyl groups in the dicarboxylic acid linker degrade primarily via ester bond hydrolysis via an intermolecular mechanism and directly release Drug-amidoacid derivatives (pathway B, Scheme 1). For example, conjugates utilizing the Linker glutaric acid exhibit release half-lives of Drug of more than 100 hours in PBS pH 7.4 at 37° C. These are known as extended release Linkers.

Another example of Linkers with three or more atoms between the two carbonyls of the dicarboxylic acid is oxaglutaric acid (OGA). Conjugates utilizing the Linker oxaglutaric acid release through the intermolecular process and exhibit release half-lives of Drug of less than 10 hours (PBS, pH 7.4, 37° C.). OGA is characterized as a fast release Linker. By way of explanation and without intending to be bound by any particular theory, the oxygen atom in the OGA group, which is in an alpha position to the carbonyl forming the ester, has an electron-withdrawing effect on the ester bond between PHF and OGA, thus making it more susceptible to hydrolysis.

Tethers:

Tethers are bifunctional organic moieties of between about 50 daltons and about 300 daltons, comprising a secondary or tertiary amine. Bifunctional organic moieties are straight, branched or cyclic aliphatic alkyl groups comprising at least one heteroatom selected from N, O, and S, in addition to the secondary or tertiary amine, and $NH_2$-aryl and $NH_2$-heteroaryl groups substituted with at least one heteroatom selected from N, O, and S, the alkyl group optionally containing aryl groups. Nonlimiting examples of various tethers are listed below:

1. Amino acids

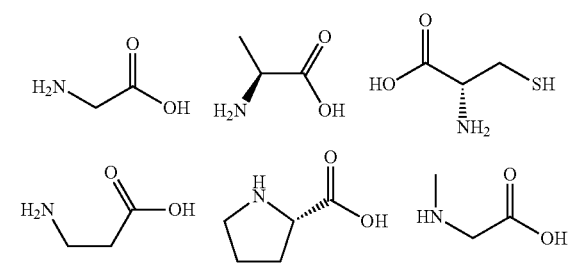

-continued
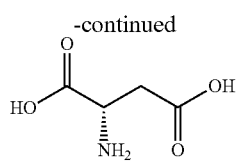
2. Aryl and Heteroaryl Groups
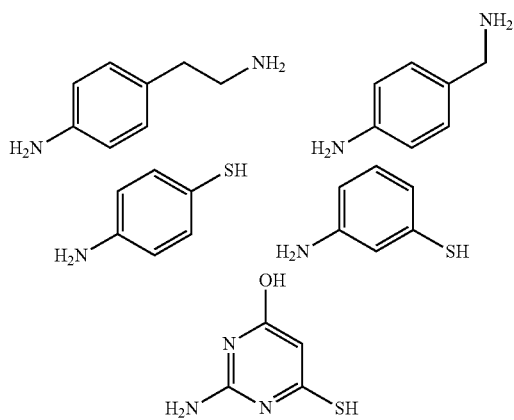
3. Heterocycles
4. Alkyl groups
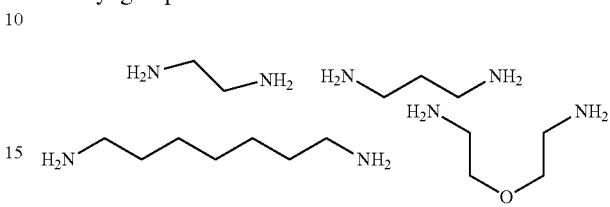
5. Cycloalkyl Groups
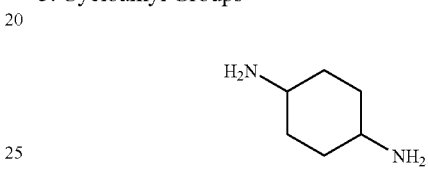
Illustrative non-limiting examples of Polyal-Drug conjugates employing various variable rate-releasing linkers are listed below:
Polyal-Fumagillol Conjugates
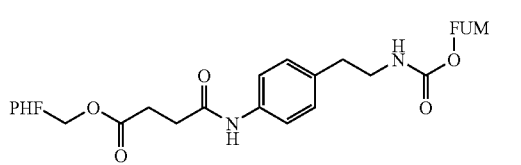
F1
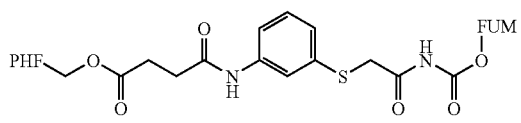
F3
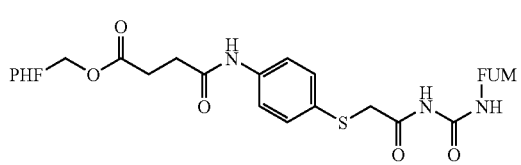
F5
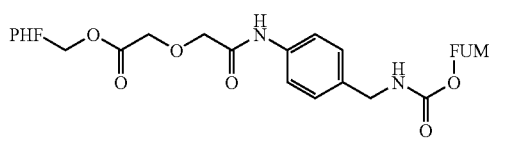
F7
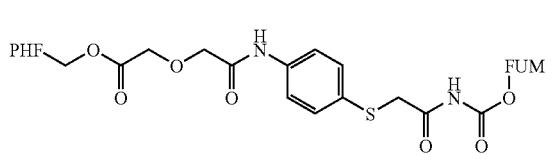
F9
F2
F4
F6
F8
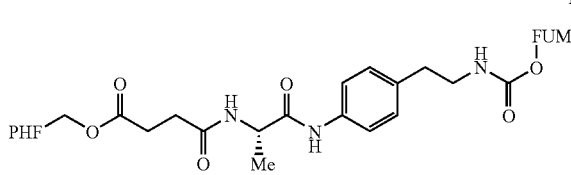
F10

-continued
F11
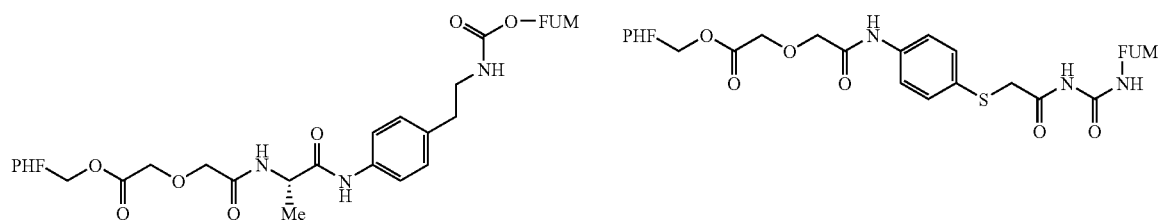
F12
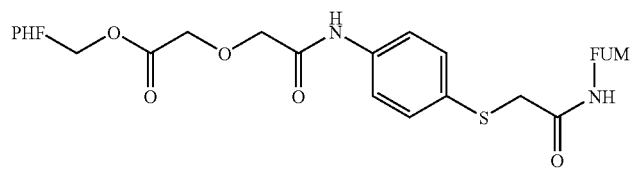
F13
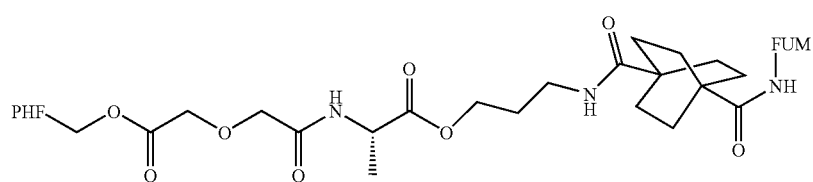
F14
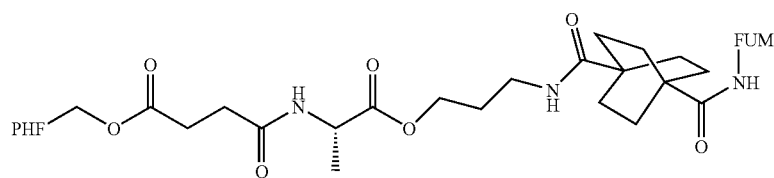
F15
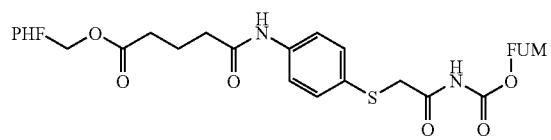
F16
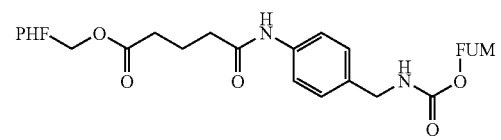
F17
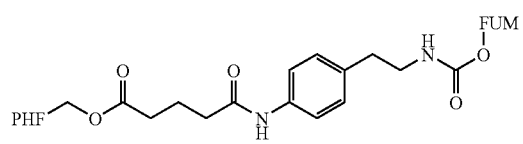
F18
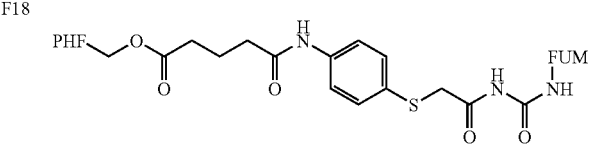
F19
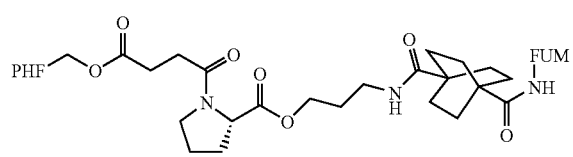
F20
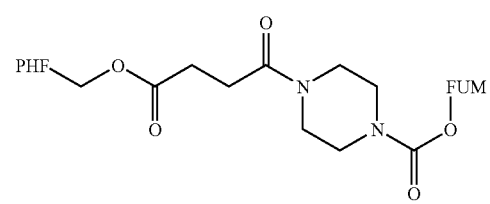
F21
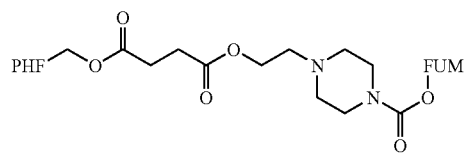
F22
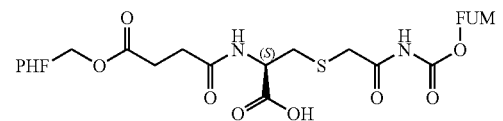
F23

Polyal-Vinca Conjugates

Compounds of the Formula III are described:

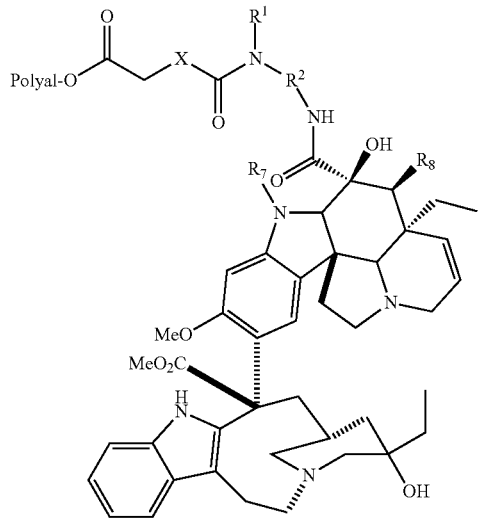

III wherein

Polyal is a polyacetal or polyketal;

X is —CH$_2$—, —OCH$_2$—, or —CH$_2$CH$_2$—, wherein one or more of —CH$_2$— is optionally substituted;

R$_1$ is H or CH$_3$;

R$_2$ is —CH(Y)—C(O)—, wherein Y is one of the side chains of the naturally occurring amino acids, an aryl group, a heteroaryl group, a cycloalkyl, an alkyl group attached to both the N—R$_1$ and the —NHC(O)— of the vinca alkaloid derivative, or a heterocycle; or R$_1$ and R$_2$, when taken together with nitrogen to which they are attached, form a ring;

R$_7$ is —CH$_3$ or —CHO; and

R$_8$ is —OCOCH$_3$ or OH.

Illustrative non-limiting examples of compounds of Formula III are listed below:

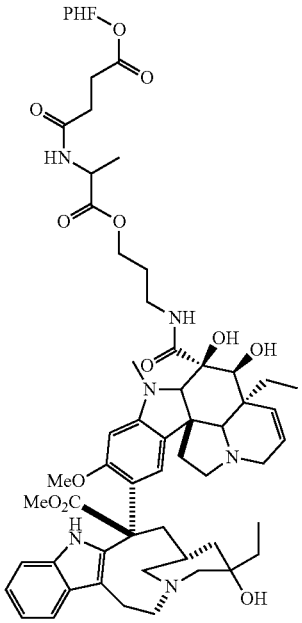

V4

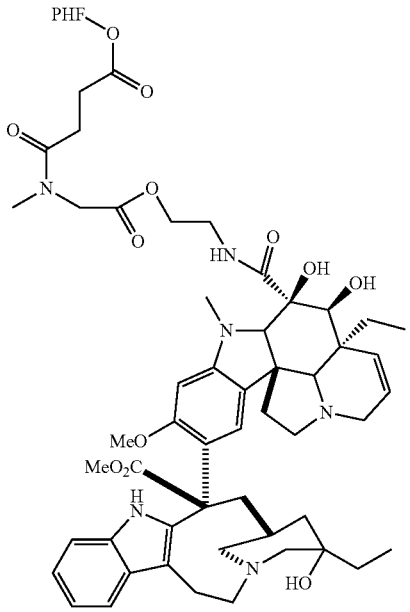

V8

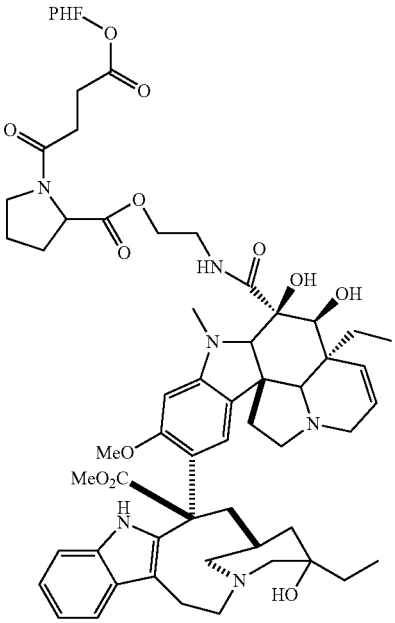

V1

-continued

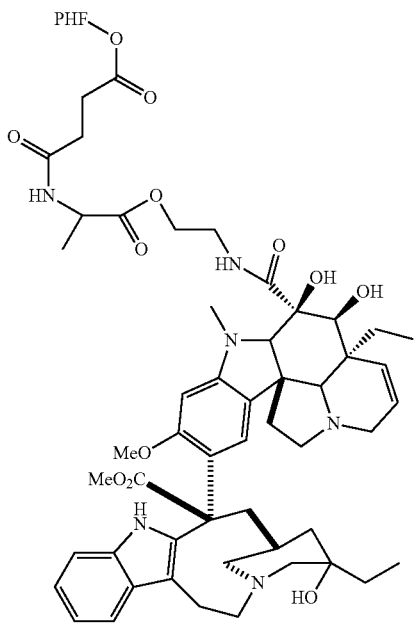

Polyal-Non-natural Camptothecin Conjugates

Compounds of the formula IV are described:

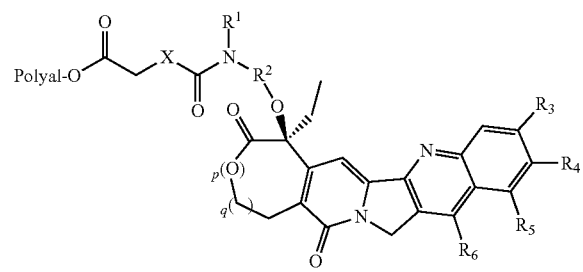

IV wherein

Polyal is a polyacetal or polyketal;

X is —CH$_2$—, —OCH$_2$—, or —CH$_2$CH$_2$—, wherein one or more of —CH$_2$— is optionally substituted;

R$_1$ is H or CH$_3$;

R$_2$ is —CH(Y)—C(O)—, wherein Y is one of the side chains of the naturally occurring amino acids, an aryl group, a heteroaryl group, a cycloalkyl, an alkyl group attached to both the N—R$_1$ and the —O— of the non-natural camptothecin derivative, or a heterocycle; or R$_1$ and R$_2$ when taken together with nitrogen to which they are attached form a ring;

R$_3$ is —H, —Cl, —F, —OH or alkyl; or R$_3$ and R$_4$, may be taken together to form a five- or six-membered ring;

R$_4$ is —H, —F, —OH, —CH$_3$, —CH=N—O-t-Butyl, —CH$_2$CH$_2$Si(CH$_3$)$_3$, or —Si((CH$_3$)$_2$)-t-Butyl;

R$_5$ is —CH$_2$—N(CH$_3$)$_2$, NH$_2$, or NO$_2$;

R$_6$ is ethyl, N-methyl piperidine, cycloalkyl, —CH$_2$CH$_2$NHCH(CH$_3$)$_2$, or —N-4-methylcyclohexylamine;

or R$_5$ and R$_6$, may be taken together to form a six-membered optionally substituted ring;

p is 0 or 1; and q is 0 or 1;

with the proviso that the compound is not PHF-SA-Gly-CPT, PHF-(methyl)SA-Gly-CPT, PHF-(2,2-dimethyl)SA-Gly-CPT, or PHF-(2-nonen-2-yl)SA-Gly-CPT.

Illustrative non-limiting examples of compounds of Formula IV are listed below:

PHF-SN38 Conjugates

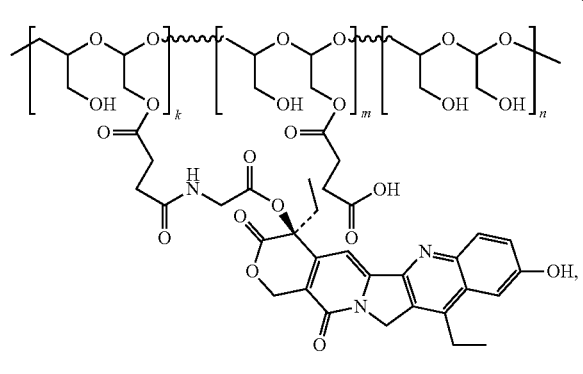

S1

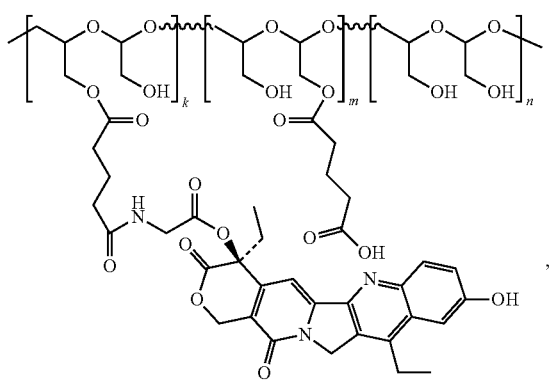

S2

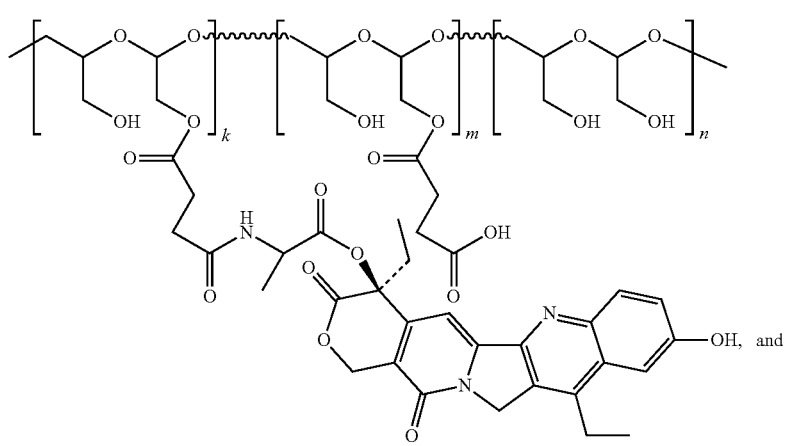

S3

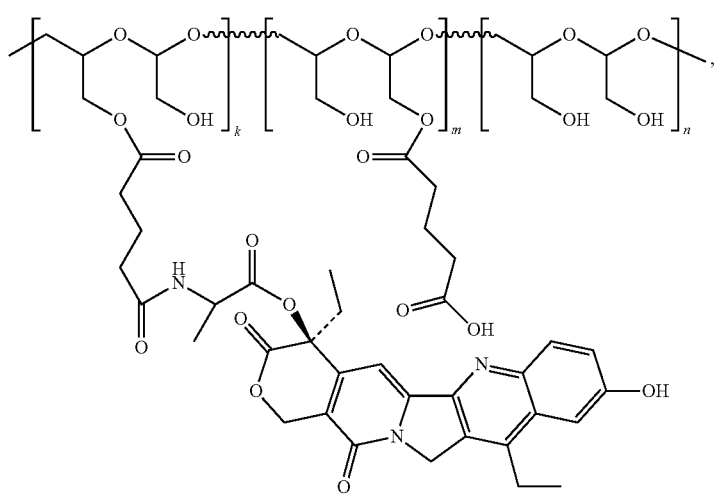

S4 wherein k ranges from 1-30, m ranges from 0-300, and n ranges from 100-750, and wherein the polyal comprises randomly distributed covalently bound monomer blocks shown in brackets; and pharmaceutically acceptable salts thereof.

Methods of Using the Polyal-Drug Conjugates Comprising Variable Rate-Releasing Linkers The rate of release of a drug from a polymeric conjugate can play a very significant role in altering the properties of the released drug, including having effects on the overall efficacy of the released drug, the duration of action of the released drug, the frequency of dosing required, the toxicity of the released drug, the biodistribution of the released drug, and the overall pharmacokinetic and pharmacodynamic properties of the released drug. For example, a slow, continuous release of a drug from a polymeric conjugate can mimic the effect of a slow, continuous infusion of the drug. Such a delivery can be beneficial, for example, with a drug-release product which has an inherently short-half life, and therefore would require much more frequent dosing if administered directly, without the benefit of conjugation to a polymer. Furthermore, a polymer conjugate of a drug release product could be designed to alter the $C_{max}$ of a drug-release product. By carefully designing a polymer conjugate with an appropriate release half-life, a $C_{max}$ value can be targeted such that it falls within a desired therapeutic window. For example, a $C_{max}$ value lower than a value known to have an associated toxicity for a known drug, while maintaining an exposure level known to be a therapeutic level of the drug-release product.

In another aspect, compositions comprising polyal-non-natural camptothecin conjugates or a pharmaceutically acceptable salt of a polyal-non-natural camptothecin conjugate and a pharmaceutically acceptable carrier are provided.

In another aspect, methods of treating cancer, comprising administering to a subject in need thereof a polyal-non-natural camptothecin conjugate or a pharmaceutically acceptable salt of a polyal-non-natural camptothecin conjugate in an amount effective to treat the cancer are described.

In some embodiments, the polyal-non-natural camptothecin useful for treating cancer is a PHF-non-natural camptothecin conjugate. In other embodiments, the PHF-non-natural camptothecin conjugate useful for treating cancer is PHF-SN38 conjugate.

In some embodiments, the cancer is selected from the group consisting of: anal, astrocytoma, leukemia, lymphoma, head and neck, liver, testicular, cervical, sarcoma, hemangioma, esophageal, eye, laryngeal, mouth, mesothelioma, skin, myeloma, oral, rectal, throat, bladder, breast, uterus, ovary, prostate, lung, colon, pancreas, renal, and gastric.

Therapeutic Administration of the Polyal-Non-Natural Camptothecin Conjugates

When administered to a subject, the polyal-non-natural camptothecin conjugates or pharmaceutically acceptable salts of the polyal-non-natural camptothecin conjugates can be administered as a component of a composition that comprises a physiologically acceptable carrier or vehicle. The compositions described herein can be prepared using a method comprising admixing the polyal-non-natural camptothecin conjugates or a pharmaceutically acceptable salt of the polyal-non-natural camptothecin conjugates and a physiologically acceptable carrier, excipient, or diluent. Admixing can be accomplished using methods well known for admixing a polyal-non-natural camptothecin conjugates or a pharmaceutically acceptable salt of the polyal-non-natural camptothecin conjugates and a physiologically acceptable carrier, excipients, or diluents.

The polyal-non-natural camptothecin conjugates or pharmaceutically acceptable salts of polyal-non-natural camptothecin conjugates can be administered by any convenient route, for example, by infusion or bolus injection and can be administered together with another therapeutic agent. Administration of the polyal-non-natural camptothecin conjugate will result in release of a non-natural camptothecin into the bloodstream.

In one embodiment, the polyal-non-natural camptothecin conjugate or a pharmaceutically acceptable salt of the polyal-non-natural camptothecin conjugate is administered intravenously.

In another aspect, compositions comprising polyal-vinca alkaloid conjugates or a pharmaceutically acceptable salt of a polyal-vinca alkaloid conjugate and a pharmaceutically acceptable carrier are provided.

In another aspect, methods of treating cancer, comprising administering to a subject in need thereof a polyal-vinca alkaloid conjugate or a pharmaceutically acceptable salt of a polyal-vinca alkaloid conjugate in an amount effective to treat the cancer are described.

In some embodiments, the polyal-vinca alkaloid conjugate useful for treating cancer is a PHF-vinca alkaloid conjugate.

In some embodiments, the cancer is selected from the group consisting of: anal, astrocytoma, leukemia, lymphoma, head and neck, liver, testicular, cervical, sarcoma, hemangioma, esophageal, eye, laryngeal, mouth, mesothelioma, skin, myeloma, oral, rectal, throat, bladder, breast, uterus, ovary, prostate, lung, colon, pancreas, renal, and gastric.

Therapeutic Administration of the Polyal-Vinca Alkaloid Conjugates

When administered to a subject, the polyal-vinca alkaloid conjugates or pharmaceutically acceptable salts of the polyal-vinca alkaloid conjugates can be administered as a component of a composition that comprises a physiologically acceptable carrier or vehicle. The compositions described herein can be prepared using a method comprising admixing the polyal-vinca alkaloid conjugates or a pharmaceutically acceptable salt of the polyal-vinca alkaloid conjugates and a physiologically acceptable carrier, excipient, or diluent. Admixing can be accomplished using methods well known for admixing a polyal-vinca alkaloid conjugates or a pharmaceutically acceptable salt of the polyal-vinca alkaloid conjugates and a physiologically acceptable carrier, excipients, or diluents.

The polyal-vinca alkaloid conjugates or pharmaceutically acceptable salts of polyal-vinca alkaloid conjugates can be administered by any convenient route, for example, by infusion or bolus injection and can be administered together with another therapeutic agent. Administration of the polyal-vinca alkaloid conjugate will result in release of a vinca alkaloid into the bloodstream.

In one embodiment, the polyal-vinca alkaloid conjugate or a pharmaceutically acceptable salt of the polyal-vinca alkaloid conjugate is administered intravenously.

Methods of Making Various Polyal-Drug Conjugates Comprising Variable Rate-Releasing Linkers The polyal-drug conjugates comprising variable rate-releasing linkers and their pharmaceutically acceptable salts can be prepared using a variety of methods starting from commercially available compounds, known compounds, or compounds prepared by known methods. The polyal-drug conjugates comprising variable rate-releasing linkers can be prepared using a variety of methods starting from commercially available compounds, known compounds, or compounds prepared by known methods. General synthetic routes to many of the compounds described are included in the following schemes. It is understood by those skilled in the art that protection and deprotection steps not shown in the Schemes may be required for these syntheses, and that the order of steps may be changed to accommodate functionality in the target molecule.

Methods useful for making the polyal-drug conjugates comprising variable rate-releasing linkers are set forth in the Examples below and generalized in the following schemes.

Scheme 3

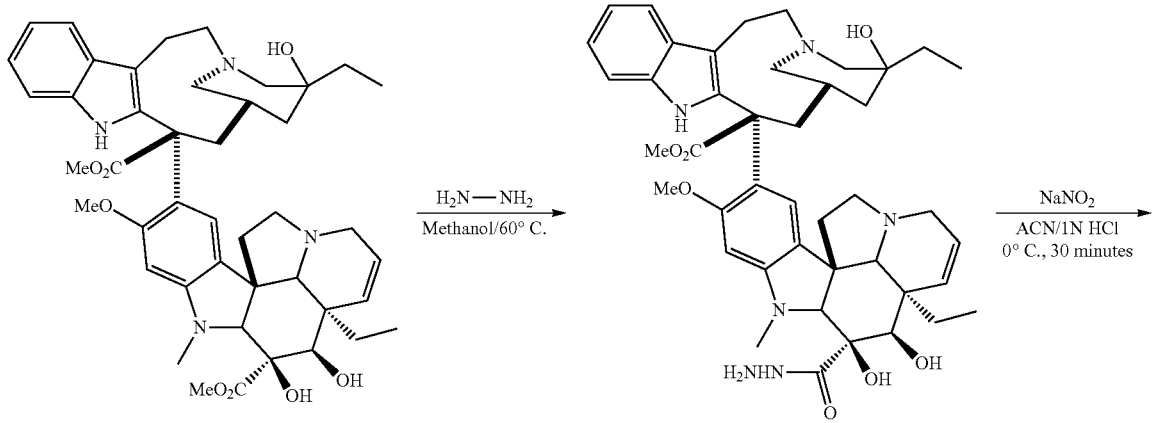

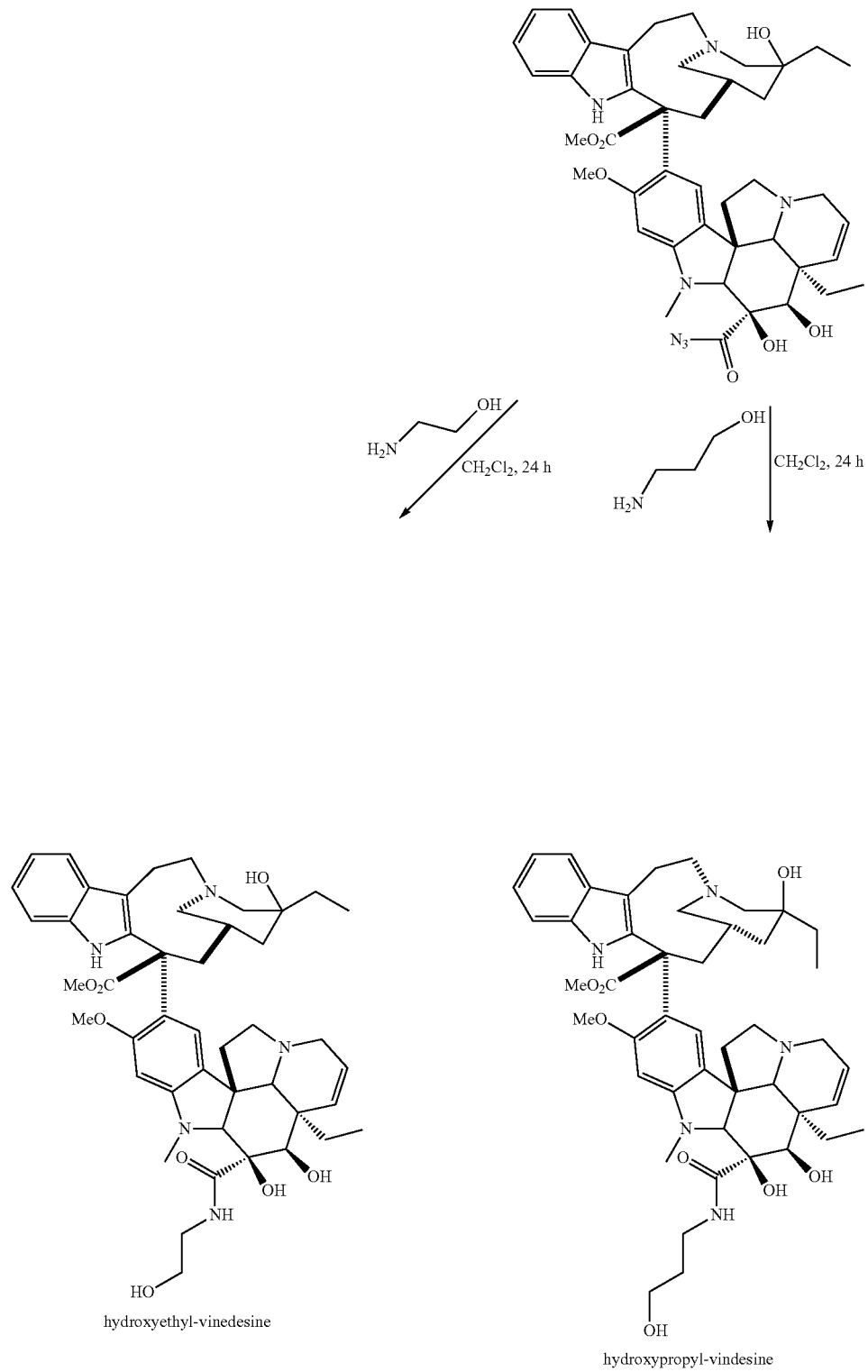

Reaction of the $C_{23}$ ester of a vinca alkaloid with hydrazine followed by treatment of the resulting product with $NaNO_2$ results in an active azido ester. Reaction of the azido ester with an amino tether such as ethanolamine or propanolamine results in a vinca alkaloid derivative with a functionalized hydroxyl which can be further derivatized with amino containing tethers for conjugation to a polyal through a dicarboxylic acid (see Scheme 2).

Scheme 4

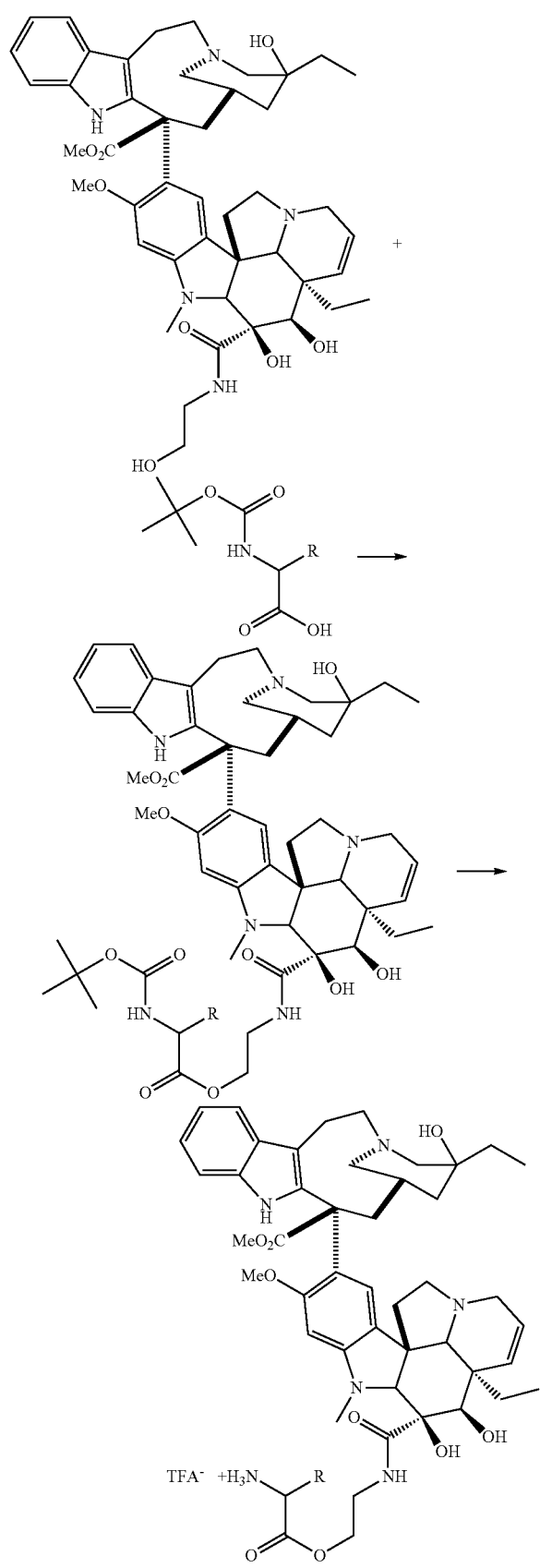

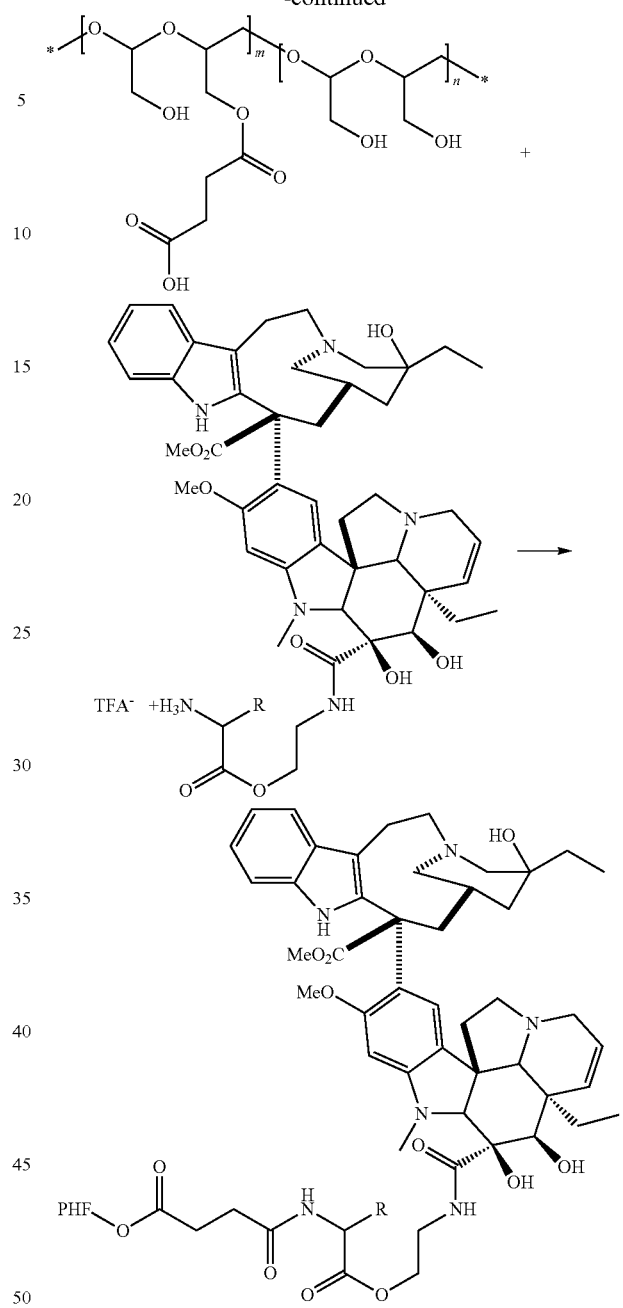

wherein m and n are 0-300, and 100-750, respectively.

Treatment of the hydroxyl derivative of the vinca alkaloid with a protected amino containing tether such as t-butoxy esterified amino acid followed by TFA hydrolysis of the ester affords the triflate salt of the vinca alkaloid. Conjugation of the vinca alkaloid to the polyals derivatized previously with a dicarboxylic acid, as reported in U.S. 2007/019008, is effected with the use of an activating agent such as EDC in water/acetonitrile as solvent. After completion, DI water was added so that the ACN is less than 10% of total the volume and the product was purified by gel filtration column (Sephadex G-25, water as eluent).

Scheme 5

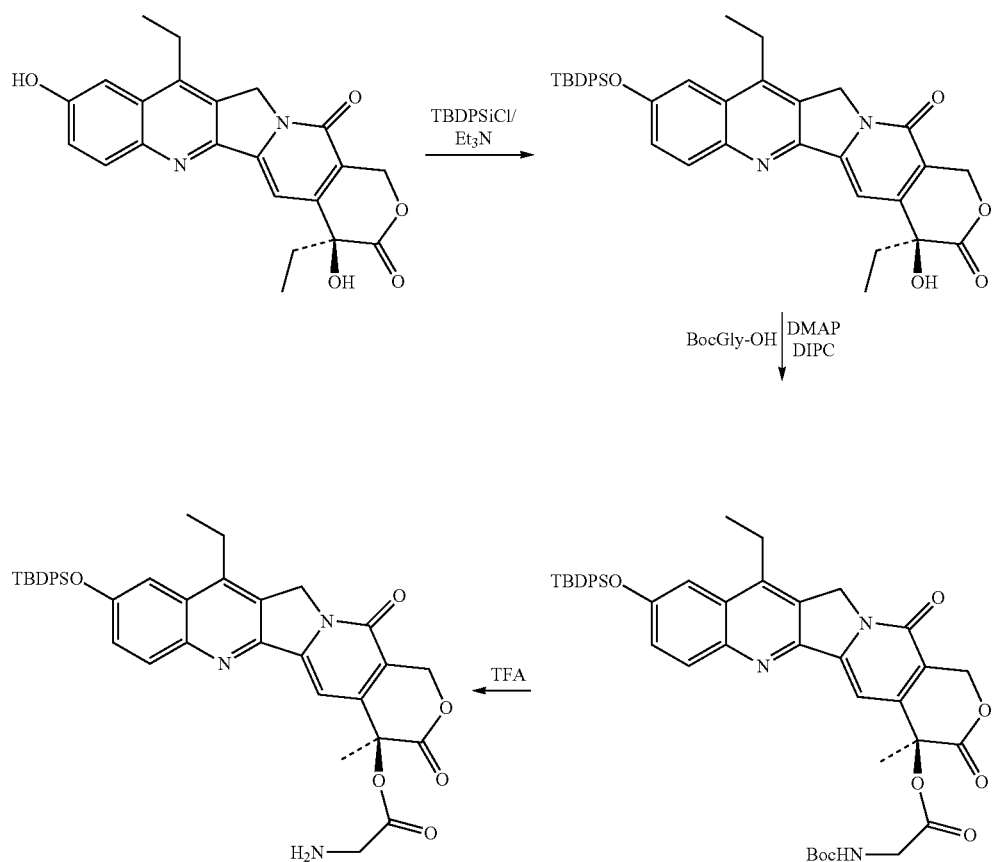

The 10-hydroxy group of non-natural camptothecin derivative, for example, SN38, is selectively protected by reacting the derivative with tert-butyldiphenylsilyl chloride in the presence of triethylamine. Subsequent glycination of the 20-hydroxy group by reacting with t-butyl-carbonyl-glycine to form the glycinate of the derivative is prepared according to Sapra, P. et al., Clin. Cancer Res., 14: 1888-1896 (2008). Alternatively, other amino acids can be employed, e.g. alanine, which slows the release half-life from the polyal. The primary amine is unmasked by removing the Boc protecting group by treatment with trifluoroacetic acid, followed by removing the TBDPS protecting group with tetrabutylammonium fluoride (see Scheme 6 below).

Scheme 6

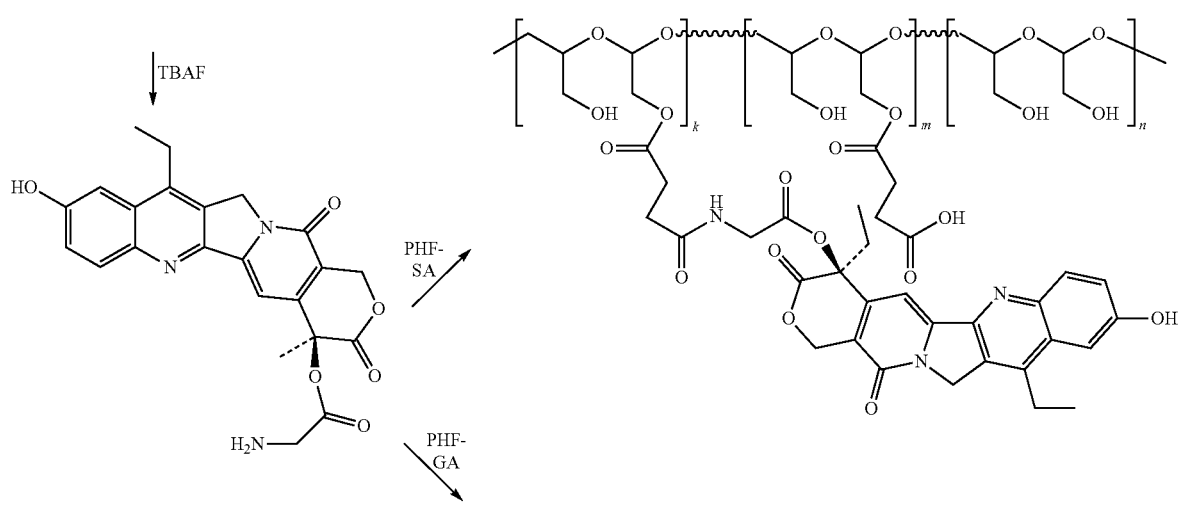

-continued

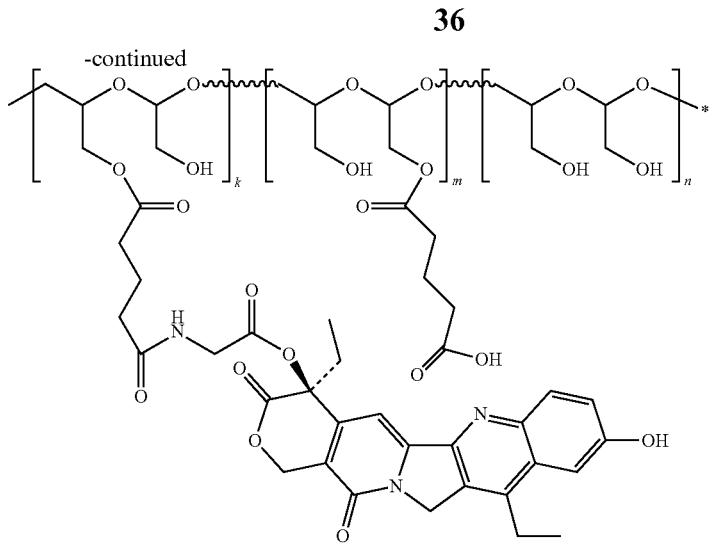

wherein k, m, and n are integers between 1-30, 0-300, and 100-750, respectively.

The resulting non-natural camptothecin-Gly derivative is then coupled with the polyal PHF activated with a dicarboxylic acid such as SA, GA, or OGA, to form the desired polyal-non-natural camptothecin conjugate PHF-SN38.

PHF-Fumagillol Conjugates

The methods for making various polyal-fumagillol conjugates which comprise variable rate-releasing linkers can be found in U.S. Ser. No. 12/276,856, the contents of which are hereby incorporated in its entirety.

EXAMPLES

Example 1

PHF-Vinca Conjugate (Conjugate V4)

Hydroxylpropylvindesine-alanine-BOC

Hydroxylpropylvindesine (0.227 g, 0.280 mmol), prepared according to the method of Conrad et al., *J. Med. Chem.* 22, 391, (1979), Boc-alanine (0.058 g, 0.308 mmol) and DMAP (3.42 mg, 0.028 mmol) were dissolved in 5 mL of anhydrous DCM (5 ml) and cooled to 0° C. DIPC (0.056 ml, 0.363 mmol) was then added and stirred at 0° C. for 3 hours. Afterwards, the reaction mixture was washed with conc. NaHCO$_3$ solution and water, dried with Na$_2$SO$_4$, filtered and finally concentrated. The crude product was added to a silica gel column and eluted with an ethyl acetate triethylamine gradient (A. ethyl acetate, B 1% triethylamine in methanol,— the gradient: 100% A for 3 minutes, 0-40% B in 10 minutes) (combiflash system, 40 g silica column).

Hydroxylpropylvindesine-alanine-TFA

Hydroxylpropylvindesine-alanine-BOC (0.227 g, 0.231 mmol) was dissolved in 2 mL 50/50 DCM/TFA, stirred at room temperature for 2 hours. Afterwards, diethylether was added to the solution to precipitate the product. The product was collected by centrifuge and the solvent decanted.

Conjugate V4

PHF-SA (1.600 g, 6.05 mmol) was dissolved in 20 mL DI water and 4 mL ACN and cooled to 0° C. Hydroxylpropylvindesine-alanine-TFA (0.21 g, 0.242 mmol) was dissolved in 2 mL ACN and added to the solution. The pH was adjusted to about 6 and then EDC (0.116 g, 0.605 mmol) was added. The solution was stirred at 0° C. for 30 minutes and then warm to r.t. The progress of reaction was monitored by HPLC (both SEC and RP). After completion, DI water was added so that the ACN is less than 10% of total the volume and the product was purified by gel filtration column (Sephadex G-25, water as eluent).

Example 2

Method for the Determination of Drug Release from PHF-Drug Conjugates In Vitro

The evaluation of the process of drug release from PHF-drug conjugates was carried out in physiological conditions in vitro. The testing was performed in phosphate buffered saline (0.05M phosphate pH 7.4, NaCl 0.9%) at 37° C., typically over a 24-hour period. The concentration of conjugated drug was monitored by high pressure size exclusion chromatography and the concentration of drug release product(s) was monitored by reverse phase HPLC using specrtophotometric detection at a wavelength specific for the drug conjugate, the drug release product, or a combination of both. The drug conjugate linker degradation rates (K, h$^{-1}$) were estimated by linear regression analysis of the conjugated drug semilogarithmic concentration decay profiles. Linker stability was reported as drug release half-lives (t ½, h, where t½ was calculated as Ln(2)/K).

TABLE 1

Release Half-lives of Various PHF-Vinca Alkaloid Drug Conjugates

| ## | Vinca Alkaloid Conjugate | T 1/2, h |
|---|---|---|
| V1 | | 3.4 |
| V2 | | 17 |
| V3 | | 19 |
| V4 | | 24 |
| V5 | | 26 |
| V6 | | 65 |
| V7 | | 75 |
| V8 | | 81 |

TABLE 1-continued

Release Half-lives of Various PHF-Vinca Alkaloid Drug Conjugates

| ## | Vinca Alkaloid Conjugate | T 1/2, h |
|---|---|---|
| V9 | PHF-O-CH(CH2CH(CH3)2)-C(=O)-HN-Vinca (leucine linker) | 200 |
| V10 | PHF-O-C(=O)-CH2CH2-C(=O)-N(proline)-C(=O)-O-CH2CH2CH2-NH-Vinca | 250 |
| V11 | PHF-O-C(=O)-CH2CH2-C(=O)-N(proline)-C(=O)-O-CH2CH2-NH-Vinca | 360 |
| V12 | PHF-O-C(=O)-CH2CH2-C(=O)-N(CH3)-Vinca | 500 |
| V13 | PHF-O-C(=O)-CH2CH2-C(=O)-N(proline)-C(=O)-O-CH2CH2-NH-Vinca | 375 |
| V14 | PHF-O-C(=O)-CH2CH2-C(=O)-N(proline)-C(=O)-O-CH2CH2CH2-NH-Vinca | — |

Vinca represents a vinca alkaloid attached to the NH through the carboxylic acid at position C-23 of the vinca alkaloid.
TABLE 2
Release Half-lives of Various PHF-Fumagillol Analog Conjugates
| | Fumagillol Analog Conjugates | $T_{1/2}$ h |
|---|---|---|
| F1 | 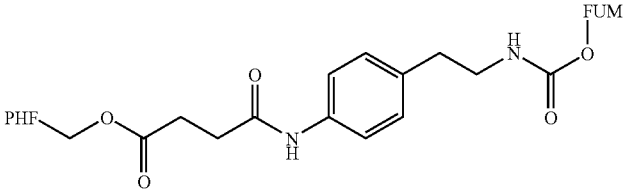 | 0.6 |
| F2 | 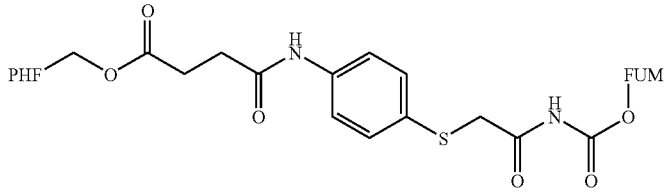 | 1.0 |
| F3 | 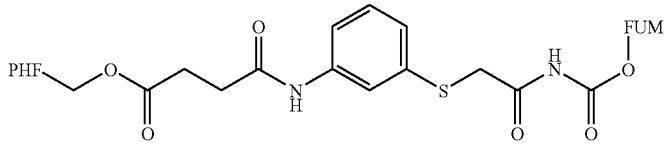 | 1.2 |
| F4 | 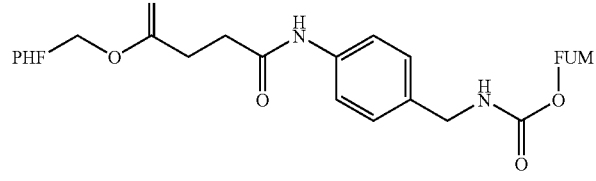 | 1.2 |
| F5 | 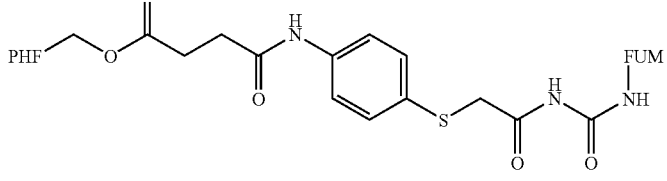 | 1.4 |
| F6 | 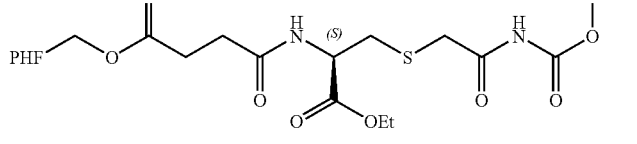 | 1-4 |
| F7 | 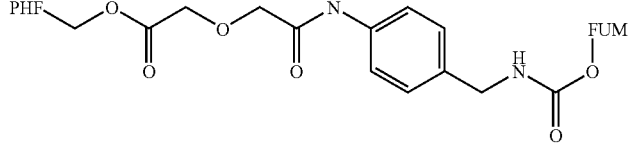 | 5.5 |

TABLE 2-continued

Release Half-lives of Various PHF-Fumagillol Analog Conjugates

| Fumagillol Analog Conjugates | $T_{1/2}$ h |
|---|---|
| F8 (structure) | 5.5 |
| F9 (structure) | 7.5 |
| F10 (structure) | 8.1 |
| F11 (structure) | 8.1 |
| F12 (structure) | 9.1 |
| F13 (structure) | 9.5 |
| F14 (structure) | 7-10 |

TABLE 2-continued
Release Half-lives of Various PHF-Fumagillol Analog Conjugates
| Fumagillol Analog Conjugates | $T_{1/2}$ h |
|---|---|
| F15 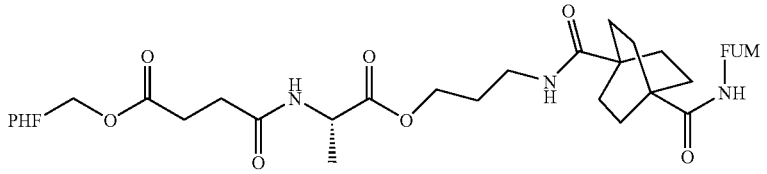 | 20 |
| F16 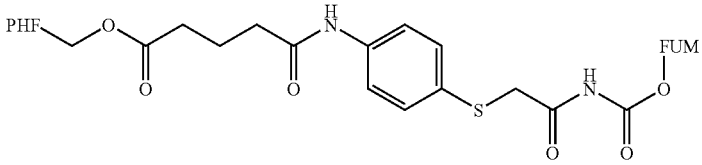 | 100 |
| F17 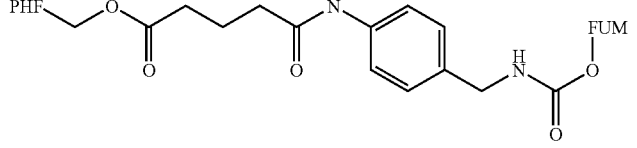 | >100 |
| F18 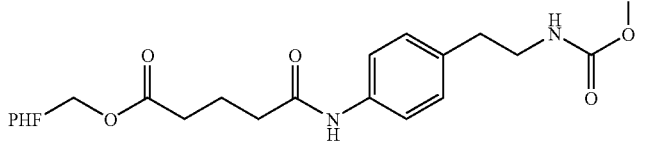 | 500 |
| F19 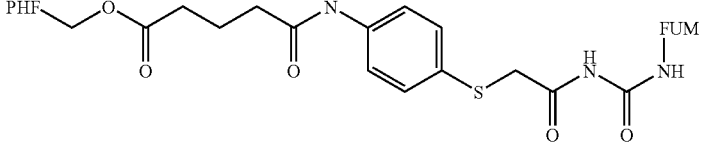 | >>200 |
| F20 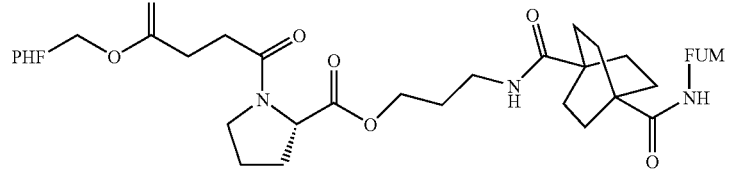 | >100 |
| F21 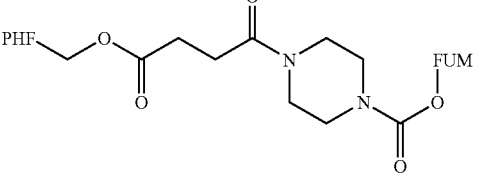 | >100 |
| F22 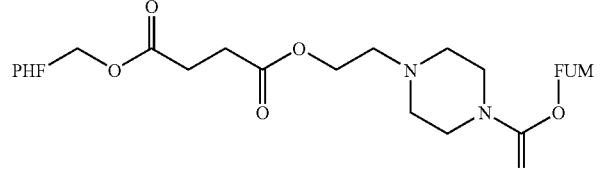 | >100 |

TABLE 2-continued

Release Half-lives of Various PHF-Fumagillol Analog Conjugates

| | Fumagillol Analog Conjugates | $T_{1/2}$ h |
|---|---|---|
| F23 | 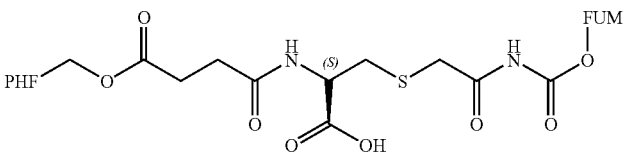 | 9.1 |

FUM means

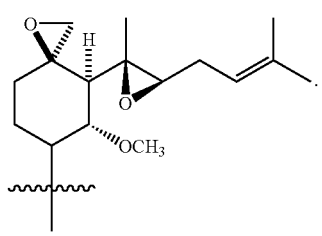 [SMILES: *C1CC[C@]2(CO2)[C@@H]([C@@]2(C)O[C@@H]2CC=C(C)C)[C@@H]1OC]

TABLE 3

Release Half-lives of Various SN38 Conjugates

| ## | SN38 Conjugate | T½, h |
|---|---|---|
| S1 | PHF-SA-Gly-SN38 | 2.0 |
| S2 | PHF-GA-Gly-SN38 | 18.5 |
| S3 | PHF-SA-Ala-SN38 | 36.9 |
| S4 | PHF-GA-Ala-SN38 | 54.2 |

Method for the Determination of Drug Release from PHF-Drug Conjugates In Vitro

Plasma incubation was carried out in buffered plasma from mouse or human. Plasma was buffered to pH 7.4 with 0.5M Phosphate buffer pH 7.2 at a ratio of 5:1 (v/v, plasma:buffer). A mixture of the PHF-drug conjugate in plasma was prepared at 0.8 mg/ml, aliquoted into 50 μl samples in microcentrifuge vials and samples were transferred to a water bath at 37° C. At time points 0, 20, 40, 60, 80, 100, 120, 140, 160, 180, 200, 220 and 240 minutes, aliquots were removed at the time point and extracted with 200 μl acetonitrile and analyzed by RP-HPLC/MS (Column Gemini C18, 150×2.0 mm, 3 μm, operating at room temperature, with an LC flow of 350 μl/min; mobile phases were: 0.1% formic acid in water (A), and 0.1% formic acid in acetonitrile, linear gradient was 10-50% B in 9.5 minutes, 50-90% B in 0.5 min, held at 90% B for 1 minute, re-equilibrated for 5 minutes at 10% B). UV integration at 365 nm of all the release products was performed after confirmation of the release products by MS. Data is shown as individual UV area peaks of the release products and the sum of them all in FIGS. 2-3, 5-6, 8-9, and 11-12.

Identification of Release Products In Vitro by Mass Spectrometry in Buffer and Plasma Release products of PHF-SN38 in PBS buffer and in human and mouse plasma were identified by mass spectrometry in acetonitrile extracts after precipitation of the polymer with acetonitrile in incubation media as described above. Results are shown in FIGS. 1-12.

Example 3

Inhibitory Effect of Polyal-SN38 Conjugates and Analogs on Cell Growth

Using HT-29 cells, the effect of the polyal-SN38 conjugates on cell growth was evaluated.

Cells are grown in McCoy's 5a medium with 1.5 mM L-glutamine supplemented with 10% FBS. The (exponentially growing) cells are seeded in 24-well culture plates (about 10000 cells/well), cultured for 24 hours, and then treated with test compounds at various dilutions. Growth inhibition is assessed 72 hours post treatment (MTT assay). The results are shown in Table 4.

TABLE 4

| Compound | HT29 IC50 (uM) | HCT116 IC50 (uM) |
|---|---|---|
| SN38-ALA-GA | 0.121 | 0.024 |
| SN38-ALA-SI | 0.457 | 0.12 |
| SN38-ALA-SA | 0.187 | 0.055 |
| SN38-GLY-SA | 0.117 | 0.032 |
| SN38-GLY-SI | 0.097 | 0.02 |
| SN38-GLY-GA | 0.126 | 0.02 |
| SN38 | 0.025 | 0.009 |
| Camptothecin (CPT) | 0.083 | 0.023 |
| CPT-SI | 0.101 | 0.039 |
| Irinotecan | 4.426 | 4.654 |

Example 4

Human Lung Xenograft Studies on PHF-Vinca Alkaloid Conjugates

HRLN female mice with H460 tumor cells positioned subcutaneous in flank are treated with PHF-Vinca alkaloid conjugates. Tumor growth is monitored in parallel with positive and negative controls of paclitaxel, and saline respectively. Treatment begins when tumors reach an average size of 80-120 mg and tumor volumes are measured twice per week until animals reach an endpoint tumor size of 2 grams or 45 days, whichever comes first. Conjugates are administered as solutions in saline intravenously at dose levels of 5-50 mg/kg (expressed in Drug equivalents) on various schedules. Treatment outcomes are assessed in terms of percent tumor growth delay (% TGD), defined as the percent increase in median time to endpoint for mice treated with an agent compared to those treated with saline, or mean or median tumor volume, for mice treated with an agent compared to those treated with saline.

Example 5

Human Colon Xenograft Studies on PHF-Non-Natural Camptothecins

Figure 13:
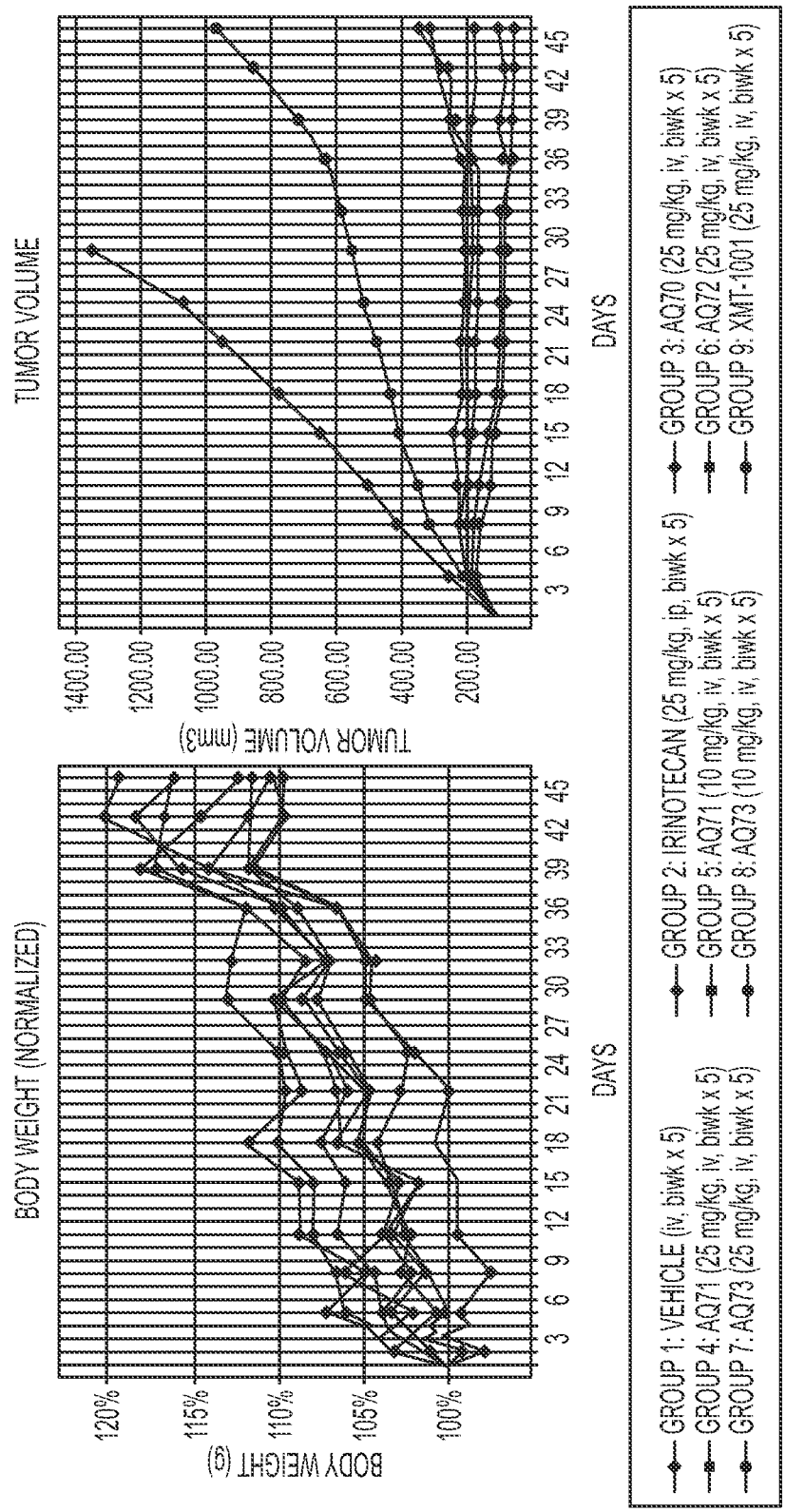
FIG. 13 depicts the responsiveness of HCT116 tumor cells treated with PHF-non-natural camptothecin conjugates as shown in terms of percent tumor growth delay (% TGD), defined as the percent increase in median time to endpoint for mice treated with an agent compared to those treated with saline, or mean or median tumor volume, for mice treated with an agent compared to those treated with saline.

HRLN female mice with HCT116 tumor cells positioned subcutaneous in flank are treated with PHF-non-natural camptothecin conjugates. Tumor growth is monitored in parallel with positive and negative controls of irinotecan, and saline respectively. Treatment begins when tumors reach an average size of 80-120 mg and tumor volumes are measured twice per week until animals reach an endpoint tumor size of 1.5 grams or 100 days, whichever comes first. Conjugates are administered as solutions in saline intravenously at dose levels of 10-25 mg/kg (expressed in Drug equivalents) on a schedule of biwk×5. Treatment outcomes are assessed in terms of percent tumor growth delay (% TGD), defined as the percent increase in median time to endpoint for mice treated with an agent compared to those treated with saline, or mean or median tumor volume, for mice treated with an agent compared to those treated with saline. The results are shown in FIG. 13.

While particular embodiments described herein have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

We claim:

1. A conjugate of Formula (I):

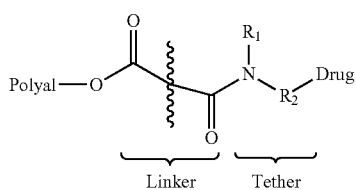

wherein

Polyal is a polyacetal or polyketal;

Linker is a dicarboxylic acid moiety containing two or more atoms between the carbonyls and —ξ— represents the two or more atoms between the carbonyl groups;

$R_1$ is H or $CH_3$;

$R_2$ is —CH(Y)—C(O)—, wherein Y is a non-hydrogen side chain of a naturally occurring amino acid; or Tether is alanine, β-alanine, sarcosine, or proline; and Drug is any organic compound with a molecular weight of between about 200 daltons and 1000 daltons, capable of covalent attachment to Tether;

wherein when Linker is a dicarboxylic acid with two atoms between the carbonyls and Tether contains a nitrogen with no reactive hydrogen, the release half-life of Drug is from about 10 h to more than about 300 h;

when Linker is a dicarboxylic acid with at least three atoms between the carbonyls and contains a heteroatom alpha to the carbonyl forming the ester, the release half-life is less than about 10 hours;

when Linker is a dicarboxylic acid with at least three atoms between the carbonyls with no heteroatom alpha to the carbonyl forming the ester, the release half-life is more than about 100 hours;

when Linker is a dicarboxylic acid with two atoms between the carbonyls and Tether contains a nitrogen with a reactive hydrogen the release half-life of Drug is from about 0.1 hours to about 24 hours; and wherein the release half-life being measured in 0.05M phosphate buffer, 0.9% saline, pH 7.4, at 37° C.

2. A conjugate of the Formula (II):

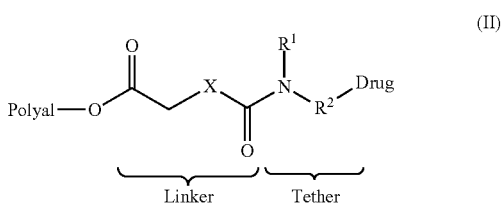

wherein

X is —$CH_2$—, —$OCH_2$—, or —$CH_2CH_2$—, wherein one or more of the $CH_2$ is optionally substituted;

$R_1$ is H or $CH_3$;

$R_2$ is —CH(Y)—C(O)—, wherein Y is a non-hydrogen side chain of a naturally occurring amino acid; or Tether is alanine, β-alanine, sarcosine, or proline;

Polyal is a polyacetal or polyketal;

Drug is any organic compound with a molecular weight of between about 200 daltons and 1000 daltons, capable of covalent attachment to Tether;

wherein when Linker is a dicarboxylic acid with two atoms between the carbonyls and Tether contains a nitrogen with no reactive hydrogen, the release half-life of Drug is from about 10 h to more than about 300 h;

when Linker is a dicarboxylic acid with at least three atoms between the carbonyls and contains a heteroatom alpha to the carbonyl forming the ester, the release half-life is less than about 10 hours;

when Linker is a dicarboxylic acid with at least three atoms between the carbonyls with no heteroatom alpha to the carbonyl forming the ester, the release half-life is more than about 100 hours;

when Linker is a dicarboxylic acid with two atoms between the carbonyls and Tether contains a nitrogen with a reactive hydrogen, the release half-life of Drug is from about 0.1 hours to about 24 hours; and wherein the release half-life being measured in 0.05M phosphate buffer, 0.9% saline, pH 7.4, at 37° C.

3. The conjugate of claim 2, wherein Polyal is a polyacetal.

4. The conjugate of claim 2, wherein Polyal is a polyketal.

5. The conjugate of claim 3, wherein the polyacetal is poly(hydroxymethylethylene hydroxymethylformal) (PHF).

6. The conjugate of claim 2, wherein $R_1$ is H.

7. The conjugate of claim 2, wherein $R_1$ is $CH_3$.

8. The conjugate of claim 2, wherein $R_2$ is —CH(Y)—C(O)—, and Y is a non-hydrogen side chain of a naturally occurring amino acid.

9. The conjugate of claim 2, wherein X is —$CH_2$—.

10. The conjugate of claim 2, wherein X is —$OCH_2$—.

11. The conjugate of claim 2, wherein X is —$CH_2CH_2$—.

12. The conjugate of claim 2, wherein X is optionally substituted with a $C_1$-$C_6$ alkyl group.

13. The conjugate of claim 2, wherein Tether is an amino acid selected from alanine, β-alanine, sarcosine, and proline.

14. The conjugate of claim 2, wherein Drug is fumagillol.

15. The conjugate of claim 2, wherein Drug is a vinca alkaloid.

16. The conjugate of claim 2, wherein Drug is a non-natural camptothecin.

17. The conjugate of claim 16, wherein the non-natural camptothecin is SN38.

18. The conjugate of claim 17, wherein the conjugate is selected from the group consisting of

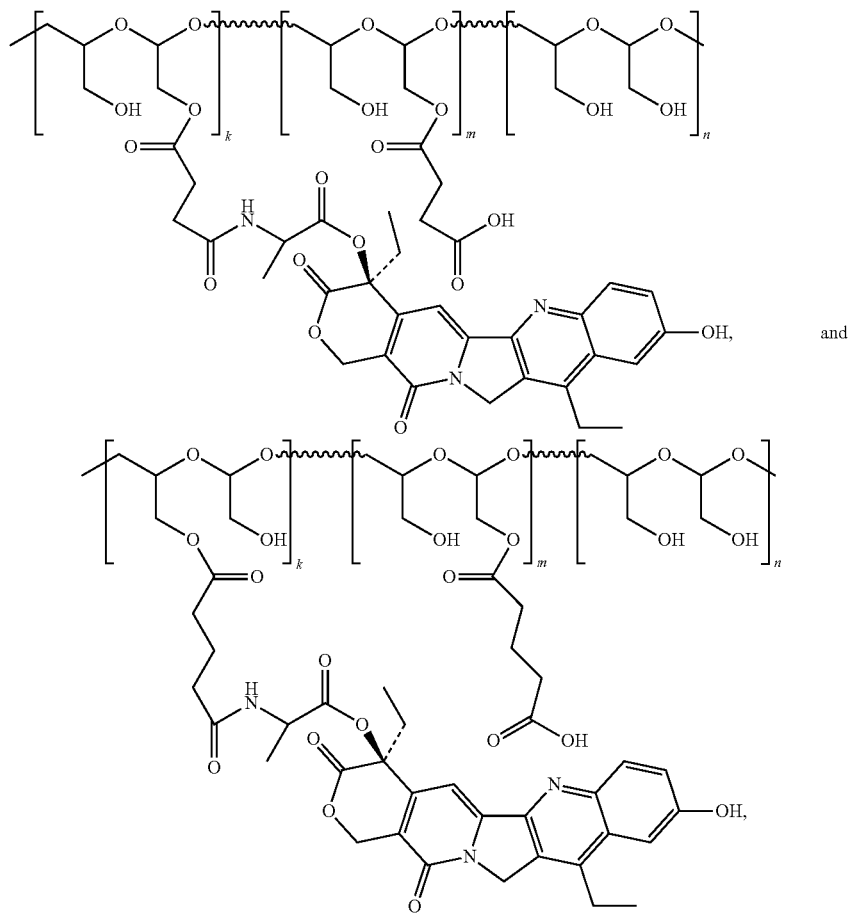

wherein k ranges from 1 to 30, m ranges from 0 to 300, and n ranges from 100 to 750, and wherein the polyal comprises randomly distributed covalently bound monomer blocks shown in brackets; and pharmaceutically acceptable salts thereof.

19. A conjugate of the Formula (III):

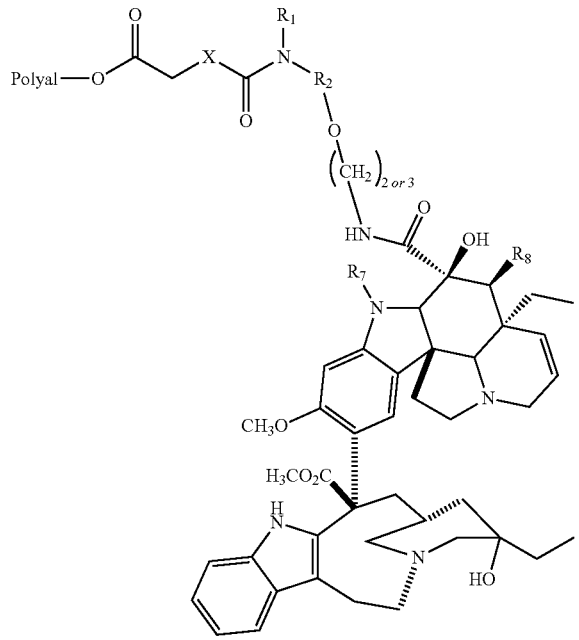

or a pharmaceutically acceptable salt thereof;
wherein
Polyal is a polyacetal or polyketal;
X is —CH$_2$—, —OCH$_2$—, or —CH$_2$CH$_2$—, wherein one or more of —CH$_2$— is optionally substituted;
R$_1$ is H or CH$_3$;
R$_2$ is —CH(Y)—C(O)—, wherein Y is a non-hydrogen side chain of a naturally occurring amino acid or —NR$_1$R$_2$— is alanine, β-alanine, sarcosine, or proline;
R$_7$ is —CH$_3$ or —CHO; and
R$_8$ is —OCOCH$_3$ or OH.

20. A conjugate of the Formula (IV):

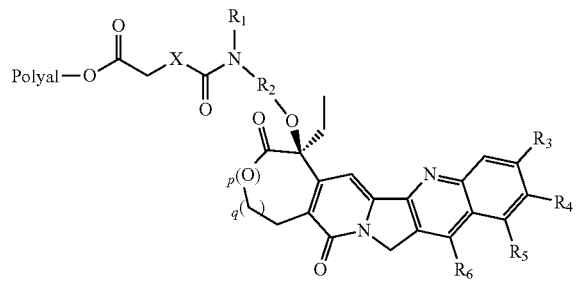

or a pharmaceutically acceptable salt;

wherein
Polyal is a polyacetal or polyketal;
X is —CH$_2$—, —OCH$_2$—, or —CH$_2$CH$_2$—, wherein one or more of —CH$_2$— is optionally substituted;
R$_1$ is H or CH$_3$;
R$_2$ is —CH(Y)—C(O)—, wherein Y is a non-hydrogen side chain of a naturally occurring amino acid; or —NR$_1$R$_2$— is alanine, β-alanine, sarcosine, or proline;
R$_3$ is —H, —Cl, —F, —OH or alkyl; or R$_3$ and R$_4$, may be taken together to form a five- or six-membered ring;
R$_4$ is —H, —F, —OH, —CH$_3$, —CH=N—O-t-Butyl, —CH$_2$CH$_2$Si(CH$_3$)$_3$, or —Si((CH$_3$)$_2$)-t-Butyl;
R$_5$ is —CH$_2$—N(CH$_3$)$_2$, NH$_2$, or NO$_2$;
R$_6$ is ethyl, N-methyl piperidine, cycloalkyl, —CH$_2$CH$_2$NHCH(CH$_3$)$_2$, or —N-4-methylcyclohexylamine;
or R$_5$ and R$_6$, may be taken together to form a six-membered optionally substituted ring;
p is 0 or 1; and
q is 0 or 1.

21. A pharmaceutical composition comprising a conjugate of the Formula (III):

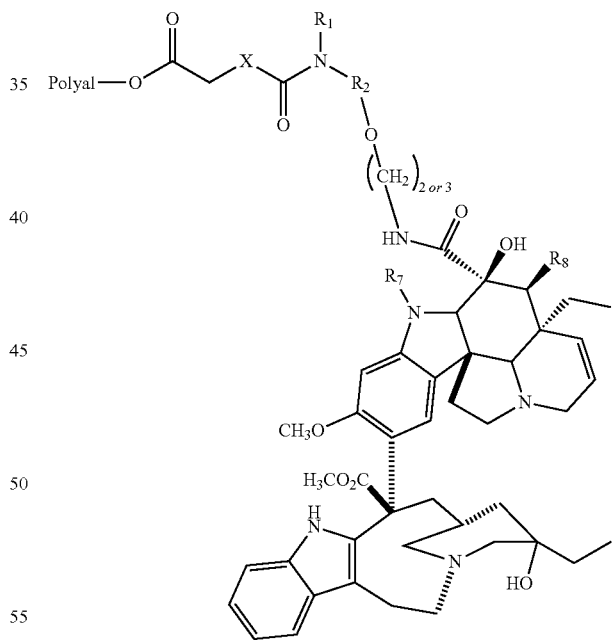

or a pharmaceutically acceptable salt thereof;
wherein
Polyal is a polyacetal or polyketal;
X is —CH$_2$—, —OCH$_2$—, or —CH$_2$CH$_2$—, wherein one or more of —CH$_2$— is optionally substituted;
R$_1$ is H or CH$_3$;

$R_2$ is —CH(Y)—C(O)—, wherein Y is a non-hydrogen side chain of a naturally occurring amino acid; or —$NR_1R_2$— is alanine, β-alanine, sarcosine, or proline;

$R_7$ is —$CH_3$ or —CHO; and $R_8$ is —$OCOCH_3$ or OH;

and a pharmaceutically acceptable carrier.

22. A method of treating cancer, comprising administering to a subject in need thereof a polyal-vinca alkaloid conjugate of Formula (III) of claim 19 or a pharmaceutically acceptable salt thereof, in an amount effective to treat the cancer.

23. The method of claim 22, wherein the polyal-vinca alkaloid conjugate of Formula III is a PHF-vinca alkaloid conjugate.

24. The method of claim 22, wherein the cancer is selected from the group consisting of anal, astrocytoma, leukemia, lymphoma, head and neck, liver, testicular, cervical, sarcoma, hemangioma, esophageal, eye, laryngeal, mouth, mesothelioma, skin, myeloma, oral, rectal, throat, bladder, breast, uterus, ovary, prostate, lung, colon, pancreas, renal, and gastric.

25. A pharmaceutical composition comprising a conjugate of Formula (IV):

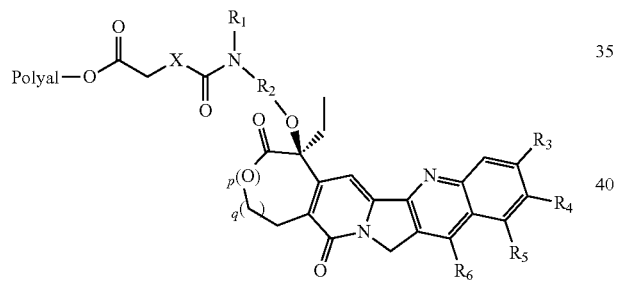

(IV)

or a pharmaceutically acceptable salt;

wherein

Polyal is a polyacetal or polyketal;

X is —$CH_2$—, —$OCH_2$—, or —$CH_2CH_2$—, wherein one or more of —$CH_2$— is optionally substituted;

$R_1$ is H or $CH_3$;

$R_2$ is —CH(Y)—C(O)—, wherein Y is a non-hydrogen side chain of a naturally occurring amino acid; or —$NR_1R_2$— is alanine, β-alanine, sarcosine, or proline;

$R_3$ is —H, —Cl, —F, —OH or alkyl; or $R_3$ and $R_4$, may be taken together to form a five- or six-membered ring;

$R_4$ is —H, —F, —OH, —$CH_3$, —CH=N—O-t-Butyl, —$CH_2CH_2Si(CH_3)_3$, or —$Si((CH_3)_2)$-t-Butyl;

$R_5$ is —$CH_2$—$N(CH_3)_2$, $NH_2$, or $NO_2$;

$R_6$ is ethyl, N-methyl piperidine, cycloalkyl, —$CH_2CH_2NHCH(CH_3)_2$, or —N-4-methylcyclohexylamine;

or $R_5$ and $R_6$, may be taken together to form a six-membered optionally substituted ring;

p is 0 or 1; and q is 0 or 1;

and a pharmaceutically acceptable carrier.

26. A method of treating cancer, comprising administering to a subject in need thereof a polyal-non-natural camptothecin conjugate of the Formula (IV) of claim 20 or a pharmaceutically acceptable salt thereof, in an amount effective to treat the cancer.

27. The method of claim 26, wherein the polyal-non-natural camptothecin of Formula IV is a PHF-non-natural camptothecin conjugate.

28. The method of claim 27, wherein the PHF-non-natural camptothecin conjugate is PHF-SN38.

29. The method of claim 26, wherein the cancer is selected from the group consisting of anal, astrocytoma, leukemia, lymphoma, head and neck, liver, testicular, cervical, sarcoma, hemangioma, esophageal, eye, laryngeal, mouth, mesothelioma, skin, myeloma, oral, rectal, throat, bladder, breast, uterus, ovary, prostate, lung, colon, pancreas, renal, and gastric.

30. The conjugate of claim 19, wherein the conjugate is selected from the group consisting of

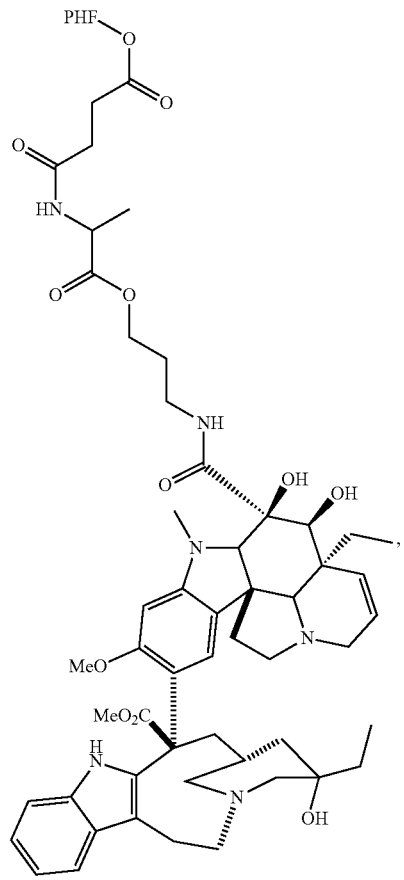

57
-continued
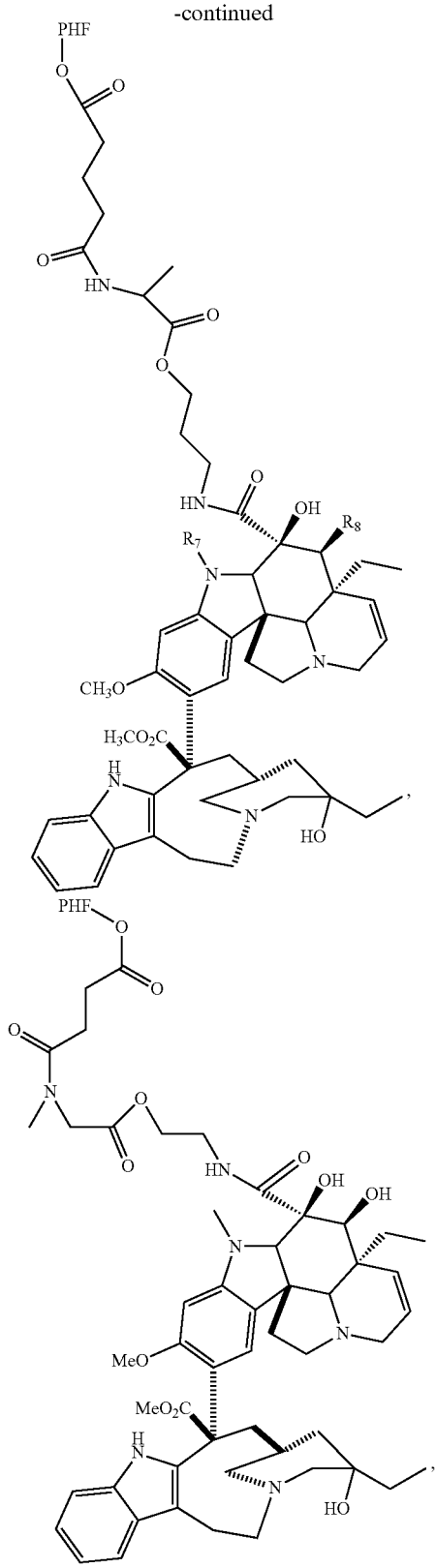
58
-continued
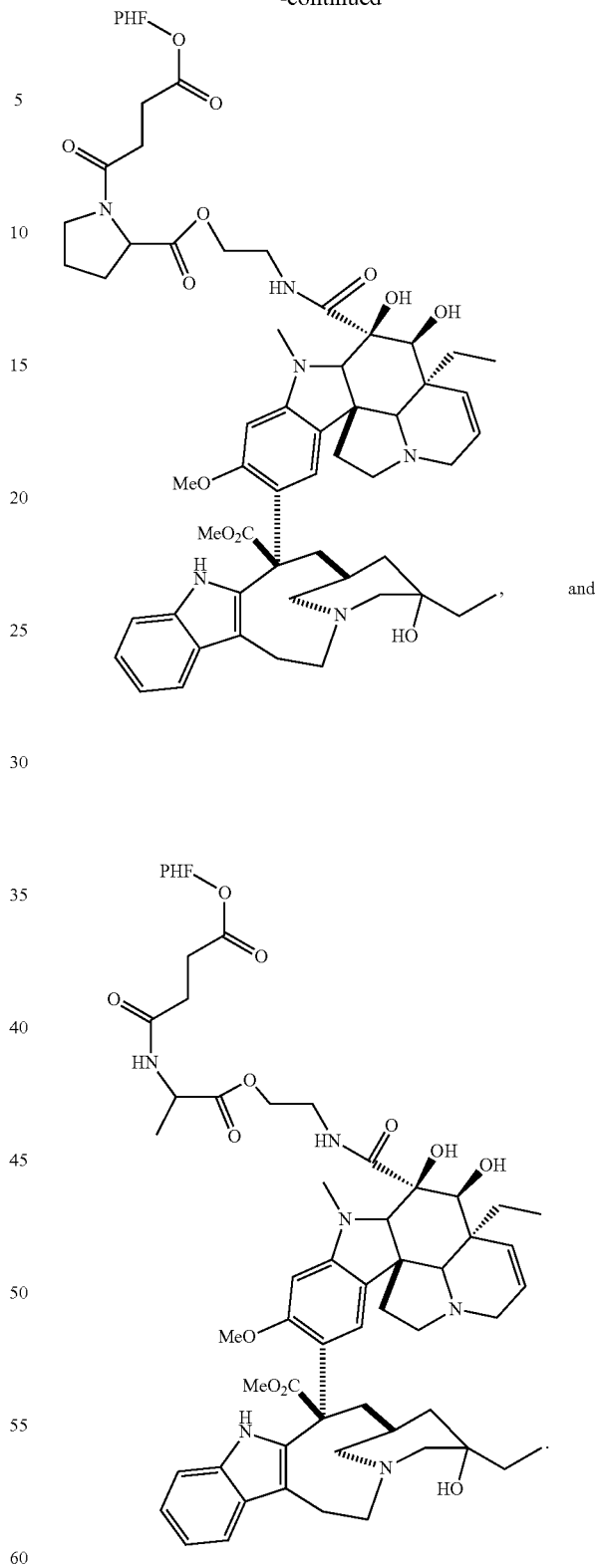
and
* * * * *